US008088905B2

(12) United States Patent
Collins et al.

(10) Patent No.: US 8,088,905 B2
(45) Date of Patent: Jan. 3, 2012

(54) NUCLEIC ACIDS ENCODING ANTIBODIES AGAINST PD-1

(75) Inventors: Mary Collins, Natick, MA (US); Clive R. Wood, Boston, MA (US); Beatriz M. Carreno, Acton, MA (US); Deborah Luxenberg, Melrose, MA (US); Jason Jussif, Salem, NH (US); Laura L. Carter, Medford, MA (US); Frances K. Bennett, Sudbury, MA (US); Viia Valge-Archer, Little Abbington (GB); John Andrews, Little Hadham Ware (GB); Caroline Russell, Herts (GB)

(73) Assignees: Wyeth, Madison, NJ (US); MedImmune Limited (GB)

( * ) Notice: Subject to any disclaimer, the term of this patent is extended or adjusted under 35 U.S.C. 154(b) by 0 days.

(21) Appl. No.: 12/405,058

(22) Filed: Mar. 16, 2009

(65) Prior Publication Data

US 2010/0028330 A1 Feb. 4, 2010

Related U.S. Application Data

(63) Continuation of application No. 10/540,084, filed as application No. PCT/IB03/06304 on Dec. 22, 2003, now Pat. No. 7,521,051.

(60) Provisional application No. 60/435,354, filed on Dec. 23, 2002.

(51) Int. Cl.
C12N 15/11 (2006.01)
(52) U.S. Cl. ...................................... 536/23.1
(58) Field of Classification Search ...................... None
See application file for complete search history.

(56) References Cited

U.S. PATENT DOCUMENTS

| 5,580,756 A | 12/1996 | Linsley et al. |
| 5,698,520 A | 12/1997 | Honjo et al. |
| 5,837,845 A | 11/1998 | Hosokawa et al. |
| 6,632,927 B2 * | 10/2003 | Adair et al. ............... 530/387.3 |
| 6,808,710 B1 * | 10/2004 | Wood et al. ............... 424/144.1 |
| 7,029,674 B2 | 4/2006 | Carreno et al. |
| 7,101,550 B2 | 9/2006 | Wood et al. |
| 7,488,802 B2 | 2/2009 | Collins et al. |
| 7,521,051 B2 | 4/2009 | Collins et al. |
| 2002/0160000 A1 | 10/2002 | Wood et al. |
| 2004/0213795 A1 | 10/2004 | Collins et al. |
| 2005/0180969 A1 | 8/2005 | Hardy et al. |
| 2006/0210567 A1 | 9/2006 | Collins et al. |
| 2007/0092504 A1 | 4/2007 | Carreno et al. |
| 2008/0311117 A1 | 12/2008 | Collins et al. |

FOREIGN PATENT DOCUMENTS

| EP | 0 945 464 A1 | 9/1999 |
| EP | 1 445 264 A1 | 8/2004 |
| JP | 4249013 B2 | 4/2009 |
| WO | WO 95/03408 A1 | 2/1995 |
| WO | WO 01/14556 A1 | 3/2001 |
| WO | WO 01/14557 A1 | 3/2001 |
| WO | WO 01/27272 A1 | 4/2001 |
| WO | WO 01/27279 A1 | 4/2001 |
| WO | WO 02/078731 A1 | 10/2002 |
| WO | WO 2004/568754 A1 | 7/2004 |

OTHER PUBLICATIONS

Rudikoff et al. 1982, Proc. Natl. Acad. Sci. USA, 79: 1979-1983.*
Panka et al., 1988, Proc. Natl. Acad. Sci. USA, 85: 3080-3084.*
Accession No. NM_008798 (2003).
Accession No. Q15116 (2003).
Agata et al., "Expression of the PD-1 Antigen on the Surface of Stimulated Mouse T and B Lymphocytes," Intl Immunol. 8:765-772 (1996).
Ansari et al., 2003, "The Programmed Death-1 (PD-1) Pathway Regulates Autoimmune Diabetes in Nonobese Diabetic (NOD) Mice," J. Exp. Med. 198: 63-69.
Attwood, Genomics. The Babel of bioinformatics. Science. Oct. 20, 2000;290(5491):471-3.
Bennett et al., 2003, "Program Death-1 Engagement Upon TCR Activation Has Distinct Effects on Costimulation and Cytokine-Driven Proliferation: Attenuation of ICOS, IL-4, and IL-21, But Not CD28, IL-7, and IL015 Responses," J. Immunol. 170: 711-718.
Blazer et al., 2002, "PD-1 Engagement Provides and Inhibitory Signal Which Downregulates T Cell Alloresponses In Vivo," Blood 100: 72a, Abstract No. 261.
Blazer et al., Infusion of Anti-B7.1 (CD80) and Anti-B7.2 (CD86) Monoclonal Antibodies Inhibits Murine Graft-Versus-Host Disease Lethality in Part Via Direct Effects on $CD4^+$ and $CD8^+$ T Cells. J Immunol. 1996;157:3250-59.
Boon et al., Human T cell responses against melanoma. Annu Rev Immunol. 2006;24:175-208.
Carreno et al., 2002, "The B7 Family of Ligands and Its Receptors: New Pathways for Costimulation and Inhibition of Immune Response," Annu. Rev. Immunol 20: 29-53.
Colman, Effects of amino acid sequence changes on antibody-antigen interactions. Res Immunol. Jan. 1994;145(1):33-6.
Curetech Press Release, 2007, "CureTech announces receipt of a Notice of Allowance from the US Patent and Trademark Office".
Davies et al., "Affinity Improvement of Single Antibody VH Domains: Residues in All Three Hypervariable Regions Affect Antigen Binding," Immunotechnology 2:169-179 (1996).
De Kruif et al., 1995, "Selection and Application of Human Single Chain Fv Antibody Fragments from a Semi-synthetic Phage Antibody Display Library with Designed CDR3 Regions," J. Mol. Biol. 248, pp. 97-105.
Desmyter et al., 2001, "Antigen Specificity and High Affinity Binding Provided by One Single Loop of a Camel Single-Domain Antibody", The Journal of Biological Chemistry, vol. 276, No. 28, pp. 26285-26290.
Dong et al., B7-H1, a third member of the B7 family, co-stimulates T-cell proliferation and interleukin-10 secretion. Nat. Med. Dec. 1999;5(12):1365-9.
EST Database Acc. No. AA399416; zt50f01.s1 Soares ovary tumor NbHOT *Homo sapiens* cDNA clone Image:725785 3', mRNA sequence (2000).

(Continued)

*Primary Examiner* — Ilia Ouspenski
(74) *Attorney, Agent, or Firm* — Wolf, Greenfield & Sacks, P.C.

(57) ABSTRACT

This disclosure provides antibodies and antigen-binding fragments that can act as agonists and/or antagonists of PD-1 (Programmed Death 1), thereby modulating immune responses in general, and those mediated by TcR and CD28, in particular. The disclosed compositions and methods may be used for example, in treating autoimmune diseases, inflammatory disorders, allergies, transplant rejection, cancer, and other immune system disorders.

6 Claims, 9 Drawing Sheets

OTHER PUBLICATIONS

Finger et al., "The human PD-1 gene: complete cDNA, genomic organization, and developmentally regulated expression in B cell progenitors." Gene, (1997), vol. 197, pp. 177-187.

Freeman et al., Engagement of the PD-1 immunoinhibitory receptor by a novel B7 family member leads to negative regulation of lymphocyte activation. J. Exp. Med. Oct. 2, 2000;192(7):1027-34.

Genbank Accession No. AF344424; *Homo sapiens* PD-1-ligand 2 protein (PDL2) mRNA, complete cds (2001).

Genbank Accession No. AF177937; *Homo sapiens* B7-H1 mRNA, complete cds (2000).

Genbank Accession No. Q13410; Butyrophilin precursor (BT) (1997).

Henry et al., "Structure and evolution of the extended B7 family." Immunology Today, (1999), vol. 20, No. 6, pp. 285-288.

Holling et al., 2004, "Function and Regulation of MHC Class II Molecules in T-Lymphocytes: Of Mice and Men," Human Immunology 65: 282-290.

Honjo, Seppuku and autoimmunity. Science. Oct. 23, 1992;258(5082):591-2.

Huang, Structural chemistry and therapeutic intervention of protein-protein interactions in immune response, human immunodeficiency virus entry, and apoptosis. Pharmacol Ther. Jun. 2000;86(3):201-15.

Ishida. et al., 1992, "Induced expression of PD-1, a novel member of the immunoglobulin gene superfamily, upon programmed cell death," EMBO Journal, 11:11, pp. 3887-3895.

Jirholt. et al., 1998, "Exploiting sequence space: shuffling in vivo formed complementarity determining regions into a master framework," Gene, 215, pp. 471-476.

Kasai et al., Nyomon Menekigaku [Introduction to Immunology]. Kodansha. 1st Ed. 1989:41-42. Japanese.

Krummel et al., CTLA-4 engagement inhibits IL-2 accumulation and cell cycle progression upon activation of resting T cells. J. Exp. Med. Jun. 1, 1996;183(6):2533-40.

Ladner et al., 2007, "Antibodies cut down to size," Nat Biotechnol. Aug.;25(8):875-7.

Latchman et al., PD-L2 is a second ligand for PD-1 and inhibits T cell activation. Nat. Immunol. Mar. 2001,2(3):261-8.

Lederman et al., A single amino acid substitution in a common African allele of the CD4 molecule ablates binding of the monoclonal antibody, OKT4. Mol Immunol. Nov. 1991;28(11):1171-81.

Lee et al., Increased vaccine-specific T cell frequency after peptide-based vaccination correlates with increased susceptibility to in vitro stimulation but does not lead to tumor regression. J Immunol. Dec. 1, 1999;163(11):6292-300.

Levi et al., 1993, "A Complementarity-Determining Region Synthetic Peptide Acts as a Miniantibody and Neutralizes Human Immunodeficiency Virus Type 1 In Vitro," Proc. Natl. Acad. Sci., 90: 4374-4378.

Marks et al., 1992, "By-Passing Immunization: Building High Affinity Human Antibodies by Chain Shuffling," Bio/Technology, vol. 10, pp. 779783.

Nielsen et al., Melanoma vaccines: the paradox of T cell activation without clinical response. Cancer Chemother Pharmacol. 2000;46 Suppl:S62-6.

Nishimura et al., "Facilitation of βSelection and Modification of Positive Selection in the Thymus of PD-1-deficient Mice." Journal of Experimental Medicine, (2000), vol. 191, No. 5, pp. 891-897.

Nishimura et al., "PD-1 Regulates Self-Tolerance to Prevent Tissue Destruction." (1998), Journal of Investigative Dermatology, vol. 110, No. 4, p. 477, Abstr. 25.

Nishimura et al., "Development of Lupus-like Autoimmune Diseases by Disruption of the PD-1 Gene Encoding an ITIM Motif-Carrying Immunoreceptor," Immunity. 1999, vol. 11, pp. 141-151.

Nishimura et al., Developmentally regulated expression of the PD-1 protein on the surface of double-negative ($CD4^-$ $CD8^-$) thymocytes. Int lmmunol. May 1996;8(5):773-80.

Nishimura et al , Immunological studies on PD-1 deficient mice: implication of PD-1 as a negative regulator for B cell responses. Int. Immunol. Oct. 1998;10(10):1563-72.

Panka et al., Variable region framework differences result in decreased or increased affinity of variant anti-digoxin antibodies. Proc Natl Acad Sci U S A. May 1988;85(9):3080-4.

Qiu et al., 2007, "Small antibody mimetics comprising two complementarity-determining regions and a framework region for tumor targeting," Nat Biotechnol. Aug. 2007;25(8):921-9. Epub.

Reiter et al., 1999, "An Antibody Single-domain Phage Display Library of a Native Heavy Chain Variable Region: Isolation of Functional Single-domain VH Molecules with a Unique Interface," J. Mol. Biol. 290, pp. 685-698.

Riley et al., The CD28 family: a T-cell rheostat for therapeutic control of T-cell activation. Blood. Jan. 1, 2005;105(1):13-21. Epub Sep. 7, 2004.

Rudikoff et al., Single amino acid substitution altering antigen-binding specificity. Proc Natl Acad Sci U S A. Mar. 1982;79(6):1979-83.

Shinohara et al., Structure and chromosomal localization of the human PD-1 gene (PDCD1). Genomics. Oct. 1994;23(3):704-6.

Skolnick et al., From genes to protein structure and function: novel applications of computational approaches in the genomic era. Trends Biotechnol. Jan. 2000;18(1):34-9.

Söderlind et al., 2000, "Recombining germline-derived CDR sequences for creating diverse single-framework antibody libraries," Nature Biotechnology, vol. 18, pp. 852-856.

Söderlind, E. et al., 1999, "Complementarity-determining region (CDR) implantation: a theme of recombination," Immunotechnology, 4, pp. 279-285.

Vaughan et al., "Human Antibodies with Sub-nanomolar Affinities Isolated from a Large Non-immunized Phage Display Library," *Nature Biotechnology* 14:309-314 (1996).

Vibhakar et al., "Activation-Induced Expression of Human Programmed Death-1 Gene in T-Lymphocytes." Experimental Cell Research, (1997), vol. 232, pp. 25-28.

Vivier et al., "Immunoreceptor tyosin-based inhibition motifs." Immunology Today, (1997), vol. 18, pp. 286-291.

Walunas et al., CTLA-4 ligation blocks CD28-dependent T cell activation. J. Exp. Med. Jun. 1, 1996;183(6):2541-50.

Ward et al., 1989, "Binding Activities of a Repertoire of Single Immunoglobulin Variable Domains Secreted from *Escherichia coli*," Nature 341: 544-546.

Welling et al., 1991, "A Ten-Residue Fragement of an Antibody (Mini-Antibody) Directed Against Lysozyme as Ligand in Immunoaffmity Chromatography," J. Chromatography, 548: 235-242.

Williams et al., 1989 "Development of Biologically Active Peptides Based on Antibody Structure," Proc. Natl. Acad. Sci. 86: 5537-5541.

Woronicz et al., Death genes in T cells. Curt Top. Micmbiol. Immunol. 1995;200:137-46.

Zhong et al., 2004, "Suppression of expression and function of negative immune regulator PD-1 by certain pattern recognition and cytokine receptor signals associated with immune system danger," Int'l Immunology, 16:8, pp. 1181-1188.

\* cited by examiner

SEQUENCE LISTING

```
<160> NUMBER OF SEQ ID NOS: 58

<210> SEQ ID NO 1
<211> LENGTH: 384
<212> TYPE: DNA
<213> ORGANISM: Homo sapiens

<400> SEQUENCE: 1
caggtgcagc tgcaggagtc gggcccagga gtggtgaagc cttcggggac cctgtccctc        60
acctgcgcta tttctggtgg ctccatcggc tctggtggct ccatcagaag tactaggtgg       120
tggagttggg tccgccagtc cccagggaag gggctggagt ggataggcga aatctatcat       180
agtgggagca ccaactacaa cccgtccctc aagagtcgcg tcaccatatc actagacaag       240
tctaggaatc acttctccct gaggctgaac tctgtgaccg ccgcggacac ggccgtttat       300
tactgtgcga gacaggacta cggtgactcc ggcgactggt acttcgatct gtggggcaag       360
gggacaatgg tcaccgtctc ctca                                              384
```

-continued

<210> SEQ ID NO 2
<211> LENGTH: 128
<212> TYPE: PRT
<213> ORGANISM: Homo sapiens

<400> SEQUENCE: 2

Gln Val Gln Leu Gln Glu Ser Gly Pro Gly Val Val Lys Pro Ser Gly
1               5                   10                  15

Thr Leu Ser Leu Thr Cys Ala Ile Ser Gly Gly Ser Ile Gly Ser Gly
            20                  25                  30

Gly Ser Ile Arg Ser Thr Arg Trp Ser Trp Val Arg Gln Ser Pro
        35                  40                  45

Gly Lys Gly Leu Glu Trp Ile Gly Glu Ile Tyr His Ser Gly Ser Thr
    50                  55                  60

Asn Tyr Asn Pro Ser Leu Lys Ser Arg Val Thr Ile Ser Leu Asp Lys
65                  70                  75                  80

Ser Arg Asn His Phe Ser Leu Arg Leu Asn Ser Val Thr Ala Ala Asp
                85                  90                  95

Thr Ala Val Tyr Tyr Cys Ala Arg Gln Asp Tyr Gly Asp Ser Gly Asp
            100                 105                 110

Trp Tyr Phe Asp Leu Trp Gly Lys Gly Thr Met Val Thr Val Ser Ser
        115                 120                 125

<210> SEQ ID NO 3
<211> LENGTH: 330
<212> TYPE: DNA
<213> ORGANISM: Homo sapiens

<400> SEQUENCE: 3
aattttatgc tgactcagcc ccactctgtg tcggagtctc cggggaagac ggtaaccatc     60
tcctgcaccc gcagcagtgg cagcattgcc agcaactctg tgcagtggta ccagcagcgc    120
ccgggcagtt cccccaccac tgtgatctat gaggataacc aaagaccctc tggggtccct    180
gatcggttct ctggctccat cgacagctcc tccaactctg cctccctcac cgtctctgga    240
ctgaagactg aggacgaggc tgactactac tgtcagtctt ctgatagcag cgctgtggta    300
ttcggcagtg ggaccaagct gaccgtccta                                     330

<210> SEQ ID NO 4
<211> LENGTH: 110
<212> TYPE: PRT
<213> ORGANISM: Homo sapiens

<400> SEQUENCE: 4

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Ser Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Val Ser Gly
65                  70                  75                  80

Leu Lys Thr Glu Asp Glu Ala Asp Tyr Tyr Cys Gln Ser Ser Asp Ser
                85                  90                  95

Ser Ala Val Val Phe Gly Ser Gly Thr Lys Leu Thr Val Leu
            100                 105                 110

<210> SEQ ID NO 5
<211> LENGTH: 357
<212> TYPE: DNA
<213> ORGANISM: Homo sapiens

<400> SEQUENCE: 5
gaggtgcagc tggtgcagtc tggagctgag gtgaagaagc ctggggcctc agtgaaagtc      60
tcctgcaagg cttctggtta cagatttacc agctacggca tcagctgggt gcgacaggcc     120
cctggacaag ggcttgagtg gatgggatgg atcagcgctt acaatggtaa cacaaactac     180
gcacagaagc tccagggcag agtcaccatg accacagaca catccacgaa cacagcctac     240
atggagctga ggagcctgag atctgacgac acggccgtgt attactgtgc gagagacgcg     300
gattatagta gtgggtctgg gtactggggc cagggaaccc tggtcaccgt ctcctca        357

<210> SEQ ID NO 6
<211> LENGTH: 119
<212> TYPE: PRT
<213> ORGANISM: Homo sapiens

<400> SEQUENCE: 6

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Asp Tyr Ser Ser Gly Ser Gly Tyr Trp Gly Gln Gly
                100                 105                 110

Thr Leu Val Thr Val Ser Ser
        115

<210> SEQ ID NO 7
<211> LENGTH: 324
<212> TYPE: DNA
<213> ORGANISM: Homo sapiens

<400> SEQUENCE: 7
tcctatgagc tgactcagcc accctcggtg tcagtgtccc caggacagac ggccaggatc      60
acctgttctg gagatgcatt gccaaagcaa tatgcttatt ggtaccagca gaagccaggc     120
caggcccctg tgatggttat atataaagac actgagaggc cctcagggat ccctgagcga     180
ttctctggct ccagctcagg gacaaaagtc acgttgacca tcagtggagt ccaggcagaa     240
gacgaggctg actattattg tcaatcagca gacaacagta ttacttatag ggtgttcggc     300
ggagggacca aggtcaccgt ccta                                            324

<210> SEQ ID NO 8
<211> LENGTH: 108
<212> TYPE: PRT
<213> ORGANISM: Homo sapiens

<400> SEQUENCE: 8

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Met Val Ile Tyr
            35                  40                  45

Lys Asp Thr Glu Arg Pro Ser Gly Ile Pro Glu Arg Phe Ser Gly Ser
50                  55                  60

Ser Ser Gly Thr Lys Val Thr Leu Thr Ile Ser Gly Val Gln Ala Glu
65                  70                  75                  80

Asp Glu Ala Asp Tyr Tyr Cys Gln Ser Ala Asp Asn Ser Ile Thr Tyr
                85                  90                  95

Arg Val Phe Gly Gly Gly Thr Lys Val Thr Val Leu
            100                 105
```

```
<210> SEQ ID NO 9
<211> LENGTH: 357
<212> TYPE: DNA
<213> ORGANISM: Homo sapiens

<400> SEQUENCE: 9
caggtgcagc tggtgcaatc tggggctgag gtgaagaaac ctggggcctc agtgagggtt      60
tcctgcaagg catctggata caccctcacc agttactata ttcactgggt gcgacaggcc     120
cctggacaag gcttgagtg atgggaata atcaacccta gaggtgccac cataagctac      180
gcacagaagt tccagggcag agtcaccatg accaggaca cgtccacgag tacagtctac      240
atggaactga gaaacttgaa atctgaggac acggccctgt attactgtgc tactgcaggc      300
atctatggtt ttgactttga ctactggggc agaggaaccc tggtcaccgt ctcctca        357
```

```
<210> SEQ ID NO 10
<211> LENGTH: 119
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Leu Thr Ser Tyr
            20                  25                  30

Tyr Ile His Trp Val Arg Gln Ala Pro Gly Gln Gly Leu Glu Trp Met
            35                  40                  45

Gly Ile Ile Asn Pro Arg Gly Ala Thr Ile Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Arg Asn Leu Lys Ser Glu Asp Thr Ala Leu Tyr Tyr Cys
                85                  90                  95

Ala Thr Ala Gly Ile Tyr Gly Phe Asp Phe Asp Tyr Trp Gly Arg Gly
            100                 105                 110

Thr Leu Val Thr Val Ser Ser
        115
```

```
<210> SEQ ID NO 11
<211> LENGTH: 333
<212> TYPE: DNA
<213> ORGANISM: Homo sapiens

<400> SEQUENCE: 11
```

```
cagtctgccc tgactcagcc tgcctccgtg tctgggtctc ctgggcagtc gatcaccatc        60
tcctgcactg gaaccagtaa tgacgttggt ggttataatt atgtctcctg gtaccaacat       120
cacccaggca aagcccccaa actcatcatt tatgatgtca ctaaccggcc ctcaggggtt       180
tctgatcgct tctctggctc caagtctggc aacacggcct ccctgaccat ctctgggctc       240
ctggctgagg acgagggtga ttattactgc agctcataca caattgttac caatttcgag       300
gttcttttcg gcggagggac caagctgacc gtc                                     333
```

```
<210> SEQ ID NO 12
<211> LENGTH: 111
<212> TYPE: PRT
<213> ORGANISM: Homo sapiens

<400> SEQUENCE: 12

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Gly Tyr
            20                  25                  30

Asn Tyr Val Ser Trp Tyr Gln His His Pro Gly Lys Ala Pro Lys Leu
        35                  40                  45

Ile Ile Tyr Asp Val Thr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Leu Ala Glu Asp Glu Gly Asp Tyr Tyr Cys Ser Ser Tyr Thr Ile Val
                85                  90                  95

Thr Asn Phe Glu Val Leu Phe Gly Gly Gly Thr Lys Leu Thr Val
            100                 105                 110
```

```
<210> SEQ ID NO 13
<211> LENGTH: 381
<212> TYPE: DNA
<213> ORGANISM: Homo sapiens

<400> SEQUENCE: 13
caggtgcagc tgcaggagtc gggcccagga ctggtgaagc cttcacagac cctgtccctc        60
acctgcactg tctctggtgg ctccatcagc agtggtgctt attactggag ctggatccgc       120
cagcacccag ggaagggcct ggagtggatt gggtacatct attacaatgg gaacacgtac       180
tacaacccgt ccctcaggag tctagttacc atatcagtag acgcgtctaa gaaccagttc       240
tccctgaagc tgagctctgt gactgccgcg gacacggccg tctattactg tgcgagagcg       300
tctgattacg tttgggggg ttatcgttat atggatgctt ttgatatctg gggccgggga       360
accctggtca ccgtctcctc a                                                  381
```

```
<210> SEQ ID NO 14
<211> LENGTH: 127
<212> TYPE: PRT
<213> ORGANISM: Homo sapiens

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr Tyr Trp Ser Trp Ile Arg Gln His Pro Gly Lys Gly Leu Glu
        35                  40                  45
```

```
Trp Ile Gly Tyr Ile Tyr Tyr Asn Gly Asn Thr Tyr Tyr Asn Pro Ser
        50                  55                  60
Leu Arg Ser Leu Val Thr Ile Ser Val Asp Ala Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Ala Ser Asp Tyr Val Trp Gly Gly Tyr Arg Tyr Met Asp
            100                 105                 110
Ala Phe Asp Ile Trp Gly Arg Gly Thr Leu Ile Thr Val Ser Ser
            115                 120                 125
```

<210> SEQ ID NO 15
<211> LENGTH: 336
<212> TYPE: DNA
<213> ORGANISM: Homo sapiens

<400> SEQUENCE: 15

```
cagtctgtgc tgactcagcc accctcagcg tctgggaccc ccgggcagag ggtcaccatc    60
tcttgttctg gaagcaactc caacatcgga agtaattctg taaactggta ccagcagctc   120
ccaggaacgg cccccaaact cctcatctat ggtaataatc agcggccctc agggggtccct  180
gaccgattct ctggctccaa gtctggcacc tcagcctccc tggccatcag tgggctccag   240
tctgagaatg aggctgatta ttactgtgca gcatgggatg acagcctgaa tggtccggta   300
ttcggccgag ggaccaaggt caccgtccta ggtgag                            336
```

<210> SEQ ID NO 16
<211> LENGTH: 112
<212> TYPE: PRT
<213> ORGANISM: Homo sapiens

<400> SEQUENCE: 16

```
Gln Ser Val Leu Thr Gln Pro Pro Ser Ala Ser Gly Thr Pro Gly Gln
1               5                   10                  15
Arg Val Thr Ile Ser Cys Ser Gly Ser Asn Ser Asn Ile Gly Ser Asn
                20                  25                  30
Ser Val Asn Trp Tyr Gln Gln Leu Pro Gly Thr Ala Pro Lys Leu Leu
            35                  40                  45
Ile Tyr Gly Asn Asn Gln Arg Pro Ser Gly Val Pro Asp Arg Phe Ser
        50                  55                  60
Gly Ser Lys Ser Gly Thr Ser Ala Ser Leu Ala Ile Ser Gly Leu Gln
65                  70                  75                  80
Ser Glu Asn Glu Ala Asp Tyr Tyr Cys Ala Ala Trp Asp Asp Ser Leu
                85                  90                  95
Asn Gly Pro Val Phe Gly Arg Gly Thr Lys Val Thr Val Leu Gly Glu
            100                 105                 110
```

<210> SEQ ID NO 17
<211> LENGTH: 12
<212> TYPE: PRT
<213> ORGANISM: Homo sapiens

<400> SEQUENCE: 17

```
Ser Gly Gly Ser Ile Arg Ser Thr Arg Trp Trp Ser
1               5                   10
```

<210> SEQ ID NO 18
<211> LENGTH: 16
<212> TYPE: PRT

-continued

<213> ORGANISM: Homo sapiens

<400> SEQUENCE: 18

Glu Ile Tyr His Ser Gly Ser Thr Asn Tyr Asn Pro Ser Leu Lys Ser
1               5                   10                  15

<210> SEQ ID NO 19
<211> LENGTH: 13
<212> TYPE: PRT
<213> ORGANISM: Homo sapiens

<400> SEQUENCE: 19

Gln Asp Tyr Gly Asp Ser Gly Asp Trp Tyr Phe Asp Leu
1               5                   10

<210> SEQ ID NO 20
<211> LENGTH: 13
<212> TYPE: PRT
<213> ORGANISM: Homo sapiens

<400> SEQUENCE: 20

Thr Arg Ser Ser Gly Ser Ile Ala Ser Asn Ser Val Gln
1               5                   10

<210> SEQ ID NO 21
<211> LENGTH: 7
<212> TYPE: PRT
<213> ORGANISM: Homo sapiens

<400> SEQUENCE: 21

Glu Asp Asn Gln Arg Pro Ser
1               5

<210> SEQ ID NO 22
<211> LENGTH: 9
<212> TYPE: PRT
<213> ORGANISM: Homo sapiens

<400> SEQUENCE: 22

Gln Ser Ser Asp Ser Ser Ala Val Val
1               5

<210> SEQ ID NO 23
<211> LENGTH: 5
<212> TYPE: PRT
<213> ORGANISM: Homo sapiens

<400> SEQUENCE: 23

Ser Tyr Gly Ile Ser
1               5

<210> SEQ ID NO 24
<211> LENGTH: 17
<212> TYPE: PRT
<213> ORGANISM: Homo sapiens

<400> SEQUENCE: 24

Trp Ile Ser Ala Tyr Asn Gly Asn Thr Asn Tyr Ala Gln Lys Leu Gln
1               5                   10                  15

Gly

<210> SEQ ID NO 25
<211> LENGTH: 10
<212> TYPE: PRT

```
<400> SEQUENCE: 25

Asp Ala Asp Tyr Ser Ser Gly Ser Gly Tyr
1               5                   10

<210> SEQ ID NO 26
<211> LENGTH: 11
<212> TYPE: PRT
<213> ORGANISM: Homo sapiens

<400> SEQUENCE: 26

Ser Gly Asp Ala Leu Pro Lys Gln Tyr Ala Tyr
1               5                   10

<210> SEQ ID NO 27
<211> LENGTH: 7
<212> TYPE: PRT
<213> ORGANISM: Homo sapiens

<400> SEQUENCE: 27

Lys Asp Thr Glu Arg Pro Ser
1               5

<210> SEQ ID NO 28
<211> LENGTH: 11
<212> TYPE: PRT
<213> ORGANISM: Homo sapiens

<400> SEQUENCE: 28

Gln Ser Ala Asp Asn Ser Ile Thr Tyr Arg Val
1               5                   10

<210> SEQ ID NO 29
<211> LENGTH: 5
<212> TYPE: PRT
<213> ORGANISM: Homo sapiens

<400> SEQUENCE: 29

Ser Tyr Tyr Ile His
1               5

<210> SEQ ID NO 30
<211> LENGTH: 17
<212> TYPE: PRT
<213> ORGANISM: Homo sapiens

<400> SEQUENCE: 30

Ile Ile Asn Pro Arg Gly Ala Thr Ile Ser Tyr Ala Gln Lys Phe Gln
1               5                   10                  15

Gly

<210> SEQ ID NO 31
<211> LENGTH: 10
<212> TYPE: PRT
<213> ORGANISM: Homo sapiens

<400> SEQUENCE: 31

Ala Gly Ile Tyr Gly Phe Asp Phe Asp Tyr
1               5                   10

<210> SEQ ID NO 32
<211> LENGTH: 14
<212> TYPE: PRT
<213> ORGANISM: Homo sapiens
```

<400> SEQUENCE: 32

Thr Gly Thr Ser Asn Asp Val Gly Gly Tyr Asn Tyr Val Ser
1               5                   10

<210> SEQ ID NO 33
<211> LENGTH: 7
<212> TYPE: PRT
<213> ORGANISM: Homo sapiens

<400> SEQUENCE: 33

Asp Val Thr Asn Arg Pro Ser
1               5

<210> SEQ ID NO 34
<211> LENGTH: 12
<212> TYPE: PRT
<213> ORGANISM: Homo sapiens

<400> SEQUENCE: 34

Ser Ser Tyr Thr Ile Val Thr Asn Phe Glu Val Leu
1               5                   10

<210> SEQ ID NO 35
<211> LENGTH: 7
<212> TYPE: PRT
<213> ORGANISM: Homo sapiens

<400> SEQUENCE: 35

Ser Gly Ala Tyr Tyr Trp Ser
1               5

<210> SEQ ID NO 36
<211> LENGTH: 16
<212> TYPE: PRT
<213> ORGANISM: Homo sapiens

<400> SEQUENCE: 36

Tyr Ile Tyr Tyr Asn Gly Asn Thr Tyr Tyr Asn Pro Ser Leu Arg Ser
1               5                   10                  15

<210> SEQ ID NO 37
<211> LENGTH: 17
<212> TYPE: PRT
<213> ORGANISM: Homo sapiens

<400> SEQUENCE: 37

Ala Ser Asp Tyr Val Trp Gly Gly Tyr Arg Tyr Met Asp Ala Phe Asp
1               5                   10                  15

Ile

<210> SEQ ID NO 38
<211> LENGTH: 13
<212> TYPE: PRT
<213> ORGANISM: Homo sapiens

<400> SEQUENCE: 38

Ser Gly Ser Asn Ser Asn Ile Gly Ser Asn Ser Val Asn
1               5                   10

<210> SEQ ID NO 39
<211> LENGTH: 7
<212> TYPE: PRT
<213> ORGANISM: Homo sapiens

<400> SEQUENCE: 39

Gly Asn Asn Gln Arg Pro Ser
1               5

<210> SEQ ID NO 40
<211> LENGTH: 11
<212> TYPE: PRT
<213> ORGANISM: Homo sapiens

<400> SEQUENCE: 40

Ala Ala Trp Asp Ser Leu Asn Gly Pro Val
1               5                   10

<210> SEQ ID NO 41
<211> LENGTH: 288
<212> TYPE: PRT
<213> ORGANISM: Homo sapiens

<400> SEQUENCE: 41

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Phe Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 42
<211> LENGTH: 320

```
<212> TYPE: DNA
<213> ORGANISM: Homo sapiens

<400> SEQUENCE: 42
gtcagcccaa ggctgccccc tcggtcactc tgttcccgcc ctcctctgag gagcttcaag      60
ccaacaaggc cacactggtg tgtctcataa gtgacttcta cccgggagcc gtgacagtgg     120
cctggaaggc agatagcagc cccgtcaagg cgggagtgga gaccaccaca ccctccaaac     180
aaagcaacaa caagtacgcg gccagcagct atctgagcct gacgcctgag cagtggaagt     240
cccacagaag ctacagctgc caggtcacgc atgaagggag caccgtggag aagacagtgg     300
cccctacaga atgttcatag                                                 320

<210> SEQ ID NO 43
<211> LENGTH: 106
<212> TYPE: PRT
<213> ORGANISM: Homo sapiens

<400> SEQUENCE: 43

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 44
<211> LENGTH: 960
<212> TYPE: DNA
<213> ORGANISM: Homo sapiens

<400> SEQUENCE: 44
cctccaccaa gggcccatcg gtcttccccc tggcaccctc ctccaagagc acctctgggg      60
gcacagcggc cctgggctgc ctggtcaagg actacttccc cgaaccggtg acggtgtcgt     120
ggaactcagg cgccctgacc agcggcgtgc acaccttccc ggctgtccta cagtcctcag     180
gactctactc cctcagcagc gtggtgaccg tgccctccag cagcttgggc acccagacct     240
acatctgcaa cgtgaatcac aagcccagca acaccaaggt ggacaagaaa gttgagccca     300
aatcttgtga caaaactcac acatgcccac cgtgcccagc acctgaactc ctggggggac     360
cgtcagtctt cctcttcccc ccaaaaccca aggacaccct catgatctcc cggacccctg     420
aggtcacatg cgtggtggtg gacgtgagcc acgaagaccc tgaggtcaag ttcaactggt     480
acgtggacgg cgtggaggtg cataatgcca agacaaagcc gcgggaggag cagtacaaca     540
gcacgtaccg tgtggtcagc gtcctcaccg tcctgcacca ggactggctg aatggcaagg     600
agtacaagtg caaggtctcc aacaaagccc tcccagcccc catcgagaaa accatctcca     660
aagccaaagg gcagccccga gaaccacagg tgtacaccct gcccccatcc cgggaggaga     720
tgaccaagaa ccaggtcagc ctgacctgcc tggtcaaagg cttctatccc agcgacatcg     780
```

-continued

```
ccgtggagtg ggagagcaat gggcagccgg agaacaacta caagaccacg cctcccgtgc    840
tggactccga cggctccttc ttcctctata gcaagctcac cgtggacaag agcaggtggc    900
agcaggggaa cgtcttctca tgctccgtga tgcatgaggc tctgcacaac cactacacgc    960
```

<210> SEQ ID NO 45
<211> LENGTH: 330
<212> TYPE: PRT
<213> ORGANISM: Homo sapiens

<400> SEQUENCE: 45

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 46
<211> LENGTH: 366

```
<212> TYPE: DNA
<213> ORGANISM: Homo sapiens

<400> SEQUENCE: 46
ggcgcgcact ccgaggtgca gctggtgcag tctgggggag gcgtggttca gcctgggagg      60
tccctgagac tctcctgtgc agcgtctgga ttcacctttt gtagctattg gatgagctgg     120
gtccgccagg ctccagggaa ggggctgag tgggtctcag ctattagtgg tagtggtggt     180
agcacatact acgcagactc cgtgaagggc cggttcacca tctccagaga caattccaag     240
aacacgctgt atctgcaaat gaacagccta gagccgagg acacggccgt atattactgt      300
gcgaaagaga actgggggatc gtacttcgat ctctgggggc aagggaccac ggtcaccgtc     360
tcctca                                                                  366

<210> SEQ ID NO 47
<211> LENGTH: 125
<212> TYPE: PRT
<213> ORGANISM: Homo sapiens

<400> SEQUENCE: 47

Gly Ala His Ser Glu Val Gln Leu Val Gln Ser Gly Gly Gly Val Val
 1               5                  10                  15

Gln Pro Gly Arg Ser Leu Arg Leu Ser Cys Ala Ala Ser Gly Phe Thr
            20                  25                  30

Phe Ser Ser Tyr Trp Cys Asp Arg Met Ser Trp Val Arg Gln Ala Pro
        35                  40                  45

Gly Lys Gly Leu Glu Trp Val Ser Ala Ile Ser Gly Ser Gly Gly Ser
    50                  55                  60

Thr Tyr Tyr Ala Asp Ser Val Lys Gly Arg Phe Thr Ile Ser Arg Asp
65                  70                  75                  80

Asn Ser Lys Asn Thr Leu Tyr Leu Gln Met Asn Ser Leu Arg Ala Glu
                85                  90                  95

Asp Thr Ala Val Tyr Tyr Cys Ala Lys Glu Asn Trp Gly Ser Tyr Phe
            100                 105                 110

Asp Leu Trp Gly Gln Gly Thr Thr Val Thr Val Ser Ser
        115                 120                 125

<210> SEQ ID NO 48
<211> LENGTH: 332
<212> TYPE: DNA
<213> ORGANISM: Homo sapiens

<400> SEQUENCE: 48
ggcgtgcact ccgacatcgt gatgacccag tctccttcca ccctgtctgc atctgtagga      60
gacagagtca ccatcacttg ccgggccagt cagggtatta gtagctggtt ggcctggtat     120
cagcagaaac cagggagagc ccctaaggtc ttgatctata aggcatctac tttagaaagt     180
ggggtcccat caaggttcag cggcagtgga tctgggacag atttcactct caccatcagc     240
agtctgcaac ctgaagattt tgcaacttac tactgtcaac agagttacag taccccgtgg     300
acgttcggcc aggggaccaa gctggaaatc aa                                    332

<210> SEQ ID NO 49
<211> LENGTH: 112
<212> TYPE: PRT
<213> ORGANISM: Homo sapiens

<400> SEQUENCE: 49

Gly Val His Ser Asp Ile Val Met Thr Gln Ser Pro Ser Thr Leu Ser
```

```
                 1               5                  10                 15
Ala Ser Val Gly Asp Arg Val Thr Ile Thr Cys Arg Ala Ser Gln Gly
                20                 25                 30

Ile Ser Ser Trp Leu Ala Trp Tyr Gln Gln Lys Pro Gly Arg Ala Pro
                35                 40                 45

Lys Val Leu Ile Tyr Lys Ala Ser Thr Leu Glu Ser Gly Val Pro Ser
                50                 55                 60

Arg Phe Ser Gly Ser Gly Ser Gly Thr Asp Phe Thr Leu Thr Ile Ser
65                 70                 75                 80

Ser Leu Gln Pro Glu Asp Phe Ala Thr Tyr Tyr Cys Gln Gln Ser Tyr
                85                 90                 95

Ser Thr Pro Trp Thr Phe Gly Gln Gly Thr Lys Leu Glu Ile Lys Arg
               100                105                110
```

<210> SEQ ID NO 50
<211> LENGTH: 6
<212> TYPE: PRT
<213> ORGANISM: Homo sapiens

<400> SEQUENCE: 50

```
Ser Ser Tyr Trp Met Ser
1               5
```

<210> SEQ ID NO 51
<211> LENGTH: 17
<212> TYPE: PRT
<213> ORGANISM: Homo sapiens

<400> SEQUENCE: 51

```
Ala Ile Ser Gly Ser Gly Gly Ser Thr Tyr Tyr Ala Asp Ser Val Lys
1               5                  10                 15

Gly
```

<210> SEQ ID NO 52
<211> LENGTH: 9
<212> TYPE: PRT
<213> ORGANISM: Homo sapiens

<400> SEQUENCE: 52

```
Glu Asn Trp Gly Ser Tyr Phe Asp Leu
1               5
```

<210> SEQ ID NO 53
<211> LENGTH: 11
<212> TYPE: PRT
<213> ORGANISM: Homo sapiens

<400> SEQUENCE: 53

```
Arg Ala Ser Gln Gly Ile Ser Ser Trp Leu Ala
1               5                  10
```

<210> SEQ ID NO 54
<211> LENGTH: 7
<212> TYPE: PRT
<213> ORGANISM: Homo sapiens

<400> SEQUENCE: 54

```
Lys Ala Ser Thr Leu Glu Ser
1               5
```

<210> SEQ ID NO 55
<211> LENGTH: 9

```
<212> TYPE: PRT
<213> ORGANISM: Homo sapiens

<400> SEQUENCE: 55

Gln Gln Ser Tyr Ser Thr Pro Trp Thr
1               5

<210> SEQ ID NO 56
<211> LENGTH: 288
<212> TYPE: PRT
<213> ORGANISM: Homo sapiens

<400> SEQUENCE: 56

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285

<210> SEQ ID NO 57
<211> LENGTH: 321
<212> TYPE: DNA
<213> ORGANISM: Homo sapiens

<400> SEQUENCE: 57
actgtggctg caccatctgt cttcatcttc ccgccatctg atgagcagtt gaaatctgga    60
```

```
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgtta g                                              321
```

```
<210> SEQ ID NO 58
<211> LENGTH: 108
<212> TYPE: PRT
<213> ORGANISM: Homo sapiens

<400> SEQUENCE: 58

His Met Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105
```

NUCLEIC ACIDS ENCODING ANTIBODIES AGAINST PD-1

RELATED APPLICATIONS

This application is a continuation of and claims priority under 35 USC §120 of U.S. patent application Ser. No. 10/540,084, filed Apr. 7, 2006, which is now allowed, which is a national stage application of and claims priority under 35 USC §371 to PCT Application Serial No. PCT/IB2003/006304, filed Dec. 22, 2003, which claims the benefit of U.S. Provisional Application Ser. No. 60/45,354, filed Dec. 23, 2002, all of which are incorporated herein by reference in their entirety.

FIELD OF THE INVENTION

The technical field relates to modulation of immune responses regulated by the Programmed Death 1 (PD-1) receptor.

BACKGROUND OF THE INVENTION

An adaptive immune response involves activation, selection, and clonal proliferation of two major classes of lymphocytes termed T cells and B cells. After encountering an antigen, T cells proliferate and differentiate into antigen-specific effector cells, while B cells proliferate and differentiate into antibody-secreting cells.

T cell activation is a multi-step process requiring several signaling events between the T cell and an antigen-presenting cell (APC). For T cell activation to occur, two types of signals must be delivered to a resting T cell. The first type is mediated by the antigen-specific T cell receptor (TcR), and confers specificity to the immune response. The second, costimulatory, type regulates the magnitude of the response and is delivered through accessory receptors on the T cell.

A primary costimulatory signal is delivered through the activating CD28 receptor upon engagement of its ligands B7-1 or B7-2. In contrast, engagement of the inhibitory CTLA-4 receptor by the same B7-1 or B7-2 ligands results in attenuation of T cell response. Thus, CTLA-4 signals antagonize costimulation mediated by CD28. At high antigen concentrations, CD28 costimulation overrides the CTLA-4 inhibitory effect. Temporal regulation of the CD28 and CTLA-4 expression maintains a balance between activating and inhibitory signals and ensures the development of an effective immune response, while safeguarding against the development of autoimmunity.

Molecular homologues of CD28 and CTLA-4 and their B-7 like ligands have been recently identified. ICOS is a CD28-like costimulatory receptor. PD-1 (Programmed Death 1) is an inhibitory receptor and a counterpart of CTLA-4. This disclosure relates to modulation of immune responses mediated by the PD-1 receptor.

PD-1 is a 50-55 kDa type I transmembrane receptor that was originally identified in a T cell line undergoing activation-induced apoptosis.

PD-1 is expressed on T cells, B cells, and macrophages. The ligands for PD-1 are the B7 family members PD-L1 (B7-H1) and PD-L2 (B7-DC).

PD-1 is a member of the immunoglobulin (Ig) superfamily that contains a single Ig V-like domain in its extracellular region. The PD-1 cytoplasmic domain contains two tyrosines, with the most membrane-proximal tyrosine (VAYEEL in mouse PD-1) located within an ITIM (immuno-receptor tyrosine-based inhibitory motif). The presence of an ITIM on PD-1 indicates that this molecule functions to attenuate antigen receptor signaling by recruitment of cytoplasmic phosphatases. Human and murine PD-1 proteins share about 60% amino acid identity with conservation of four potential N-glycosylation sites, and residues that define the Ig-V domain. The ITIM in the cytoplasmic region and the ITIM-like motif surrounding the carboxy-terminal tyrosine (TEYATI in human and mouse) are also conserved between human and murine orthologues.

PD-1 is expressed on activated T cells, B cells, and monocytes. Experimental data implicates the interactions of PD-1 with its ligands in downregulation of central and peripheral immune responses. In particular, proliferation in wild-type T cells but not in PD-1-deficient T cells is inhibited in the presence of PD-L1. Additionally, PD-1-deficient mice exhibit an autoimmune phenotype. PD-1 deficiency in the C57BL/6 mice results in chronic progressive lupus-like glomerulonephritis and arthritis. In Balb/c mice, PD-1 deficiency leads to severe cardiomyopathy due to the presence of heart-tissue-specific self-reacting antibodies.

In general, a need exists to provide safe and effective therapeutic methods for immune disorders such as, for example, autoimmune diseases, inflammatory disorders, allergies, transplant rejection, cancer, immune deficiency, and other immune system-related disorders. Modulation of the immune responses involved in these disorders can be accomplished by manipulation of the PD-1 pathway.

SUMMARY OF THE INVENTION

The present disclosure provides antibodies that can act as agonists and/or antagonists of PD-1, thereby modulating immune responses regulated by PD-1. The disclosure further provides anti-PD-1 antibodies that comprise novel antigen-binding fragments. Anti-PD-1 antibodies of the invention are capable of (a) specifically binding to PD-1, including human PD-1; (b) blocking PD-1 interactions with its natural ligand(s); or (c) performing both functions. Furthermore, the antibodies may possess immunomodulatory properties, i.e., they may be effective in modulating the PD-1-associated downregulation of immune responses. Depending on the method of use and the desired effect, the antibodies may be used to either enhance or inhibit immune responses.

Nonlimiting illustrative embodiments of the antibodies are referred to as PD1-17, PD1-28, PD1-33, PD1-35, and PD1-F2. Other embodiments comprise a $V_H$ and/or $V_L$ domain of the Fv fragment of PD1-17, PD1-28, PD1-33, PD1-35, or PD1-F2. Further embodiments comprise one or more complementarity determining regions (CDRs) of any of these $V_H$ and $V_L$ domains. Other embodiments comprise an H3 fragment of the $V_H$ domain of PD1-17, PD1-28, PD1-33, PD1-35, or PD1-F2.

The disclosure also provides compositions comprising PD-1 antibodies, and their use in methods of modulating immune response, including methods of treating humans or animals. In particular embodiments, anti-PD-1 antibodies are used to treat or prevent immune disorders by virtue of increasing or reducing the T cell response mediated by TcR/CD28. Disorders susceptible to treatment with compositions of the invention include but are not limited to rheumatoid arthritis, multiple sclerosis, inflammatory bowel disease, Crohn's disease, systemic lupus erythematosis, type 1 diabetes, transplant rejection, graft-versus-host disease, hyperproliferative immune disorders, cancer, and infectious diseases.

Additionally, anti-PD-1 antibodies may be used diagnostically to detect PD-1 or its fragments in a biological sample. The amount of PD-1 detected may be correlated with the expression level of PD-1, which, in turn, is correlated with the activation status of immune cells (e.g., activated T cells, B cells, and monocytes) in the subject.

The disclosure also provides isolated nucleic acids, which comprise a sequence encoding a $V_H$ or $V_L$ domain from the Fv fragment of PD1-17, PD1-28, PD1-33, PD1-35, or PD1-F2. Also provided are isolated nucleic acids, which comprise a sequence encoding one or more CDRs from any of the presently disclosed $V_H$ and $V_L$ domains. The disclosure also provides vectors and host cells comprising such nucleic acids.

The disclosure further provides a method of producing new $V_H$ and $V_L$ domains and/or functional antibodies comprising all or a portion of such domains derived from the $V_H$ or $V_L$ domains of PD1-17, PD1-28, PD1-33, PD1-35, or PD1-F2.

Additional aspects of the disclosure will be set forth in part in the description which follows, and in part will be obvious from the description, or may be learned by practicing the invention. The invention is set forth and particularly pointed out in the appended claims, and the present disclosure should not be construed as limiting the scope of the claims in any way. The following detailed description includes exemplary representations of various embodiments of the invention, which are not restrictive of the invention, as claimed. The accompanying figures constitute a part of this specification and, together with the description, serve only to illustrate various embodiments and not limit the invention. Citation of references is not an admission that these references are prior art to the invention.

DETAILED DESCRIPTION

Definitions

Figure 1A:
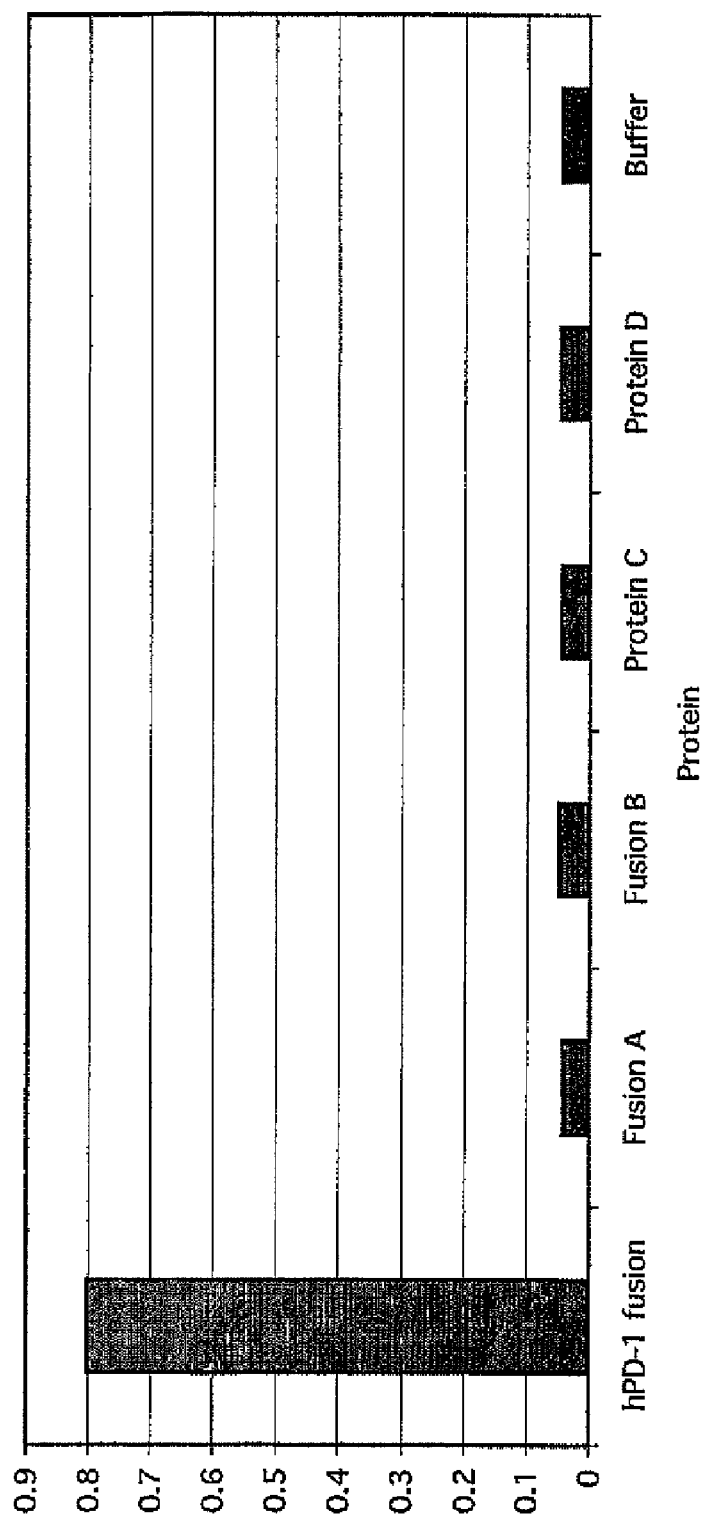
FIGS. 1A and 1B show reactivity of scFv antibodies with human PD-1 as determined by phage ELISA.

The term "antibody," as used in this disclosure, refers to an immunoglobulin or a fragment or a derivative thereof, and encompasses any polypeptide comprising an antigen-binding site, regardless whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')$_2$, Fv, scFv, Fd, dAb, and other antibody fragments that retain antigen-binding function, i.e., the ability to bind PD-1 specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant."

An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

The term "repertoire" refers to a genetically diverse collection of nucleotides derived wholly or partially from sequences that encode expressed immunoglobulins. The sequences are generated by in vivo rearrangement of, e.g., V, D, and J segments for H chains and, e.g., V and J segment for L chains. Alternatively, the sequences may be generated from a cell line by in vitro stimulation, in response to which the rearrangement occurs. Alternatively, part or all of the sequences may be obtained by combining, e.g., unrearranged V segments with D and J segments, by nucleotide synthesis, randomised mutagenesis, and other methods, e.g., as disclosed in U.S. Pat. No. 5,565,332.

The terms "specific interaction" and "specific binding" refer to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant $K_A$ is higher than $10^6$ $M^{-1}$, or more preferably higher than $10^8$ $M^{-1}$. If necessary, non-specific binding can be reduced without substantially affecting specific binding by varying the binding conditions. The appropriate binding conditions such as concentration of antibodies, ionic strength of the solution, temperature, time allowed for binding, concentration of a blocking agent (e.g., serum albumin, milk casein), etc., may be optimized by a skilled artisan using routine techniques. Illustrative conditions are set forth in Examples 1, 2, 4, 6 and 7.

The phrase "substantially as set out" means that the relevant CDR, $V_H$, or $V_L$ domain of the invention will be either identical to or have only insubstantial differences in the specified regions (e.g., a CDR), the sequence of which is set out. Insubstantial differences include minor amino acid changes, such as substitutions of 1 or 2 out of any 5 amino acids in the sequence of a specified region.

The term "PD-1 activity" refers to one or more immunoregulatory activities associated with PD-1. For example, PD-1 is a negative regulator of the TcR/CD28-mediated immune response. Procedures for assessing the PD-1 activity in vivo and in vitro are described in Examples 8, 9 and 10.

The terms "modulate," "immunomodulatory," and their cognates refer to a reduction or an increase in the activity of PD-1 associated with downregulation of T cell responses due to its interaction with an anti-PD-1 antibody, wherein the reduction or increase is relative to the activity of PD-1 in the absence of the same antibody. A reduction or an increase in activity is preferably at least about 10%, 20%, 30%, 40%, 50%, 60%, 70%, 80%, 90%, or more. When PD-1 activity is reduced, the terms "modulatory" and "modulate" are interchangeable with the terms "inhibitory" and "inhibit." When PD-1 activity is increased, the terms "modulatory" and "modulate" are interchangeable with the terms "activating"

and "activate." The activity of PD-1 can be determined quantitatively using T cell proliferation assays as described in Examples 8 and 9.

The terms "treatment" and "therapeutic method" refer to both therapeutic treatment and prophylactic/preventative measures. Those in need of treatment may include individuals already having a particular medical disorder as well as those who may ultimately acquire the disorder (i.e., those needing preventative measures).

The term "effective amount" refers to a dosage or amount that is sufficient to reduce the activity of PD-1 to result in amelioration of symptoms in a patient or to achieve a desired biological outcome, e.g., increased cytolytic activity of T cells, induction of immune tolerance, reduction or increase of the PD-1 activity associated with the negative regulation of T-cell mediated immune response, etc.

The term "isolated" refers to a molecule that is substantially free of its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

Anti-PD-1 Antibodies

The disclosure provides anti-PD-1 antibodies that comprise novel antigen-binding fragments.

In general, antibodies can be made, for example, using traditional hybridoma techniques (Kohler and Milstein (1975) Nature, 256: 495-499), recombinant DNA methods (U.S. Pat. No. 4,816,567), or phage display performed with antibody libraries (Clackson et al. (1991) Nature, 352: 624-628; Marks et al. (1991) J. Mol. Biol., 222: 581-597). For other antibody production techniques, see also Antibodies: A Laboratory Manual, eds. Harlow et al., Cold Spring Harbor Laboratory, 1988. The invention is not limited to any particular source, species of origin, method of production.

Intact antibodies, also known as immunoglobulins, are typically tetrameric glycosylated proteins composed of two light (L) chains of approximately 25 kDa each and two heavy (H) chains of approximately 50 kDa each. Two types of light chain, designated as the λ chain and the κ chain, are found in antibodies. Depending on the amino acid sequence of the constant domain of heavy chains, immunoglobulins can be assigned to five major classes: A, D, E, G and M, and several of these may be further divided into subclasses (isotypes), e.g., $IgG_1$, $IgG_2$, $IgG_3$, $IgG_4$, $IgA_1$, and $IgA_2$.

The subunit structures and three-dimensional configurations of different classes of immunoglobulins are well known in the art. For a review of antibody structure, see Harlow et al., supra. Briefly, each light chain is composed of an N-terminal variable domain ($V_L$) and a constant domain ($C_L$). Each heavy chain is composed of an N-terminal variable domain ($V_H$), three or four constant domains ($C_H$), and a hinge region. The $C_H$ domain most proximal to $V_H$ is designated as $C_H1$. The $V_H$ and $V_L$ domains consist of four regions of relatively conserved sequence called framework regions (FR1, FR2, FR3, and FR4), which form a scaffold for three regions of hypervariable sequence called complementarity determining regions (CDRs). The CDRs contain most of the residues responsible for specific interactions with the antigen. The three CDRs are referred to as CDR1, CDR2, and CDR3. CDR constituents on the heavy chain are referred to as H1, H2, and H3, while CDR constituents on the light chain are referred to as L1, L2, and L3, accordingly. CDR3 and, particularly H3, are the greatest source of molecular diversity within the antigen-binding domain. H3, for example, can be as short as two amino acid residues or greater than 26.

The Fab fragment (Fragment antigen-binding) consists of the $V_H$-$C_H1$ and $V_L$-$C_L$ domains covalently linked by a disulfide bond between the constant regions. To overcome the tendency of non-covalently linked $V_H$ and $V_L$ domains in the Fv to dissociate when co-expressed in a host cell, a so-called single chain (sc) Fv fragment (scFv) can be constructed. In a scFv, a flexible and adequately long polypeptide links either the C-terminus of the $V_H$ to the N-terminus of the $V_L$ or the C-terminus of the $V_L$ to the N-terminus of the $V_H$. Most commonly, a 15-residue $(Gly_4Ser)_3$ peptide is used as a linker but other linkers are also known in the art.

Antibody diversity is a result of combinatorial assembly of multiple germline genes encoding variable regions and a variety of somatic events. The somatic events include recombination of variable gene segments with diversity (D) and joining (J) gene segments to make a complete $V_H$ region and the recombination of variable and joining gene segments to make a complete $V_L$ region. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation.

Based on the estimated number of germline gene segments, the random recombination of these segments, and random $V_H$-$V_L$ pairing, up to $1.6 \times 10^7$ different antibodies could be produced (Fundamental Immunology, $3^{rd}$ ed., ed. Paul, Raven Press, New York, N.Y., 1993). When other processes which contribute to antibody diversity (such as somatic mutation) are taken into account, it is thought that upwards of $1 \times 10^{10}$ different antibodies could be potentially generated (Immunoglobulin Genes, $2^{nd}$ ed., eds. Jonio et al., Academic Press, San Diego, Calif., 1995). Because of the many processes involved in antibody diversity, it is highly unlikely that independently generated antibodies will have identical or even substantially similar amino acid sequences in the CDRs.

The disclosure provides novel CDRs derived from human immunoglobulin gene libraries. The structure for carrying a CDR will generally be an antibody heavy or light chain or a portion thereof, in which the CDR is located at a location corresponding to the CDR of naturally occurring $V_H$ and $V_L$. The structures and locations of immunoglobulin variable domains may be determined, for example, as described in Kabat et al., Sequences of Proteins of Immunological Interest, No. 91-3242, National Institutes of Health Publications, Bethesda, Md., 1991.

DNA and amino acid sequences of anti-PD-1 antibodies, their scFv fragment, $V_H$ and $V_L$ domains, and CDRs are set forth in the Sequence Listing and are enumerated as listed in Table 1. Particular nonlimiting illustrative embodiments of the antibodies are referred to as PD1-17, PD1-28, PD1-33, PD1-35, and PD1-F2. The positions for each CDR within the $V_H$ and $V_L$ domains of the illustrative embodiments are listed in Tables 2 and 3.

TABLE 1

DNA and Amino Acid (AA) Sequences of $V_H$ and $V_L$ Domains and CDRs

| Sequence | PD1-17 | PD1-28 | PD1-33 | PD1-35 | PD1-F2 |
|---|---|---|---|---|---|
| $V_H$ DNA | SEQ ID NO: 1 | SEQ ID NO: 5 | SEQ ID NO: 9 | SEQ ID NO: 13 | SEQ ID NO: 46 |
| $V_H$ AA | SEQ ID NO: 2 | SEQ ID NO: 6 | SEQ ID NO: 10 | SEQ ID NO: 14 | SEQ ID NO: 47 |
| $V_L$ DNA | SEQ ID NO: 3 | SEQ ID NO: 7 | SEQ ID NO: 11 | SEQ ID NO: 15 | SEQ ID NO: 48 |
| $V_L$ AA | SEQ ID NO: 4 | SEQ ID NO: 8 | SEQ ID NO: 12 | SEQ ID NO: 16 | SEQ ID NO: 49 |
| H1 AA | SEQ ID NO: 17 | SEQ ID NO: 23 | SEQ ID NO: 29 | SEQ ID NO: 35 | SEQ ID NO: 50 |
| H2 AA | SEQ ID NO: 18 | SEQ ID NO: 24 | SEQ ID NO: 30 | SEQ ID NO: 36 | SEQ ID NO: 51 |
| H3 AA | SEQ ID NO: 19 | SEQ ID NO: 25 | SEQ ID NO: 31 | SEQ ID NO: 37 | SEQ ID NO: 52 |
| L1 AA | SEQ ID NO: 20 | SEQ ID NO: 26 | SEQ ID NO: 32 | SEQ ID NO: 38 | SEQ ID NO: 53 |
| L2 AA | SEQ ID NO: 21 | SEQ ID NO: 27 | SEQ ID NO: 33 | SEQ ID NO: 39 | SEQ ID NO: 54 |
| L3 AA | SEQ ID NO: 22 | SEQ ID NO: 28 | SEQ ID NO: 34 | SEQ ID NO: 40 | SEQ ID NO: 55 |

TABLE 2

Positions of Heavy Chain CDRs

| CDR | PD1-17 SEQ ID NO: 2 | PD1-28 SEQ ID NO: 6 | PD1-33 SEQ ID NO: 10 | PD1-35 SEQ ID NO: 14 | PD1-F2 SEQ ID NO: 47 |
|---|---|---|---|---|---|
| H1 | 31-42 | 31-35 | 31-35 | 31-37 | 34-42 |
| H2 | 57-72 | 50-66 | 50-66 | 52-67 | 57-73 |
| H3 | 105-117 | 99-108 | 99-108 | 100-116 | 106-114 |

TABLE 3

Positions of Light Chain CDRs

| CDR | PD1-17 SEQ ID NO: 4 | PD1-28 SEQ ID NO: 8 | PD1-33 SEQ ID NO: 12 | PD1-35 SEQ ID NO: 16 | PD1-F2 SEQ ID NO: 49 |
|---|---|---|---|---|---|
| L1 | 23-35 | 23-33 | 23-36 | 23-35 | 28-35 |
| L2 | 51-57 | 49-55 | 52-58 | 51-57 | 54-61 |
| L3 | 92-100 | 88-98 | 91-102 | 90-100 | 94-101 |

Anti-PD-1 antibodies may optionally comprise antibody constant regions or parts thereof. For example, a $V_L$ domain may have attached, at its C terminus, antibody light chain constant domains including human Cκ or Cλ chains. Similarly, a specific antigen-binding domain based on a $V_H$ domain may have attached all or part of an immunoglobulin heavy chain derived from any antibody isotype, e.g., IgG, IgA, IgE and IgM and any of the isotype sub-classes, which include but are not limited to, $IgG_1$ and $IgG_4$. In the exemplary embodiments, PD1-17, PD1-28, PD1-33, and PD1-35, antibodies comprise C-terminal fragments of heavy and light chains of human $IgG_{1\lambda}$, while PD1-F2 comprises C-terminal fragments of heavy and light chains of human $IgG_{1\kappa}$. The DNA and amino acid sequences for the C-terminal fragment of are well known in the art (see, e.g., Kabat et al., Sequences of Proteins of Immunological Interest, No. 91-3242, National Institutes of Health Publications, Bethesda, Md., 1991). Non-limiting exemplary sequences are set forth in Table 4.

TABLE 4

| C-Terminal Region | DNA | Amino acid |
|---|---|---|
| IgG1 heavy chain | SEQ ID NO: 44 | SEQ ID NO: 45 |
| λ light chain | SEQ ID NO: 42 | SEQ ID NO: 43 |
| κ light chain | SEQ ID NO: 57 | SEQ ID NO: 58 |

Certain embodiments comprise a $V_H$ and/or $V_L$ domain of an Fv fragment from PD1-17, PD1-28, PD1-33, PD1-35, and PD1-F2. Further embodiments comprise at least one CDR of any of these $V_H$ and $V_L$ domains. Antibodies, comprising at least one of the CDR sequences set out in SEQ ID NO:2, SEQ ID NO:4, SEQ ID NO:6, SEQ ID NO:8, SEQ ID NO:10, SEQ ID NO:12, SEQ ID NO:14, SEQ ID NOs:16-40, SEQ ID NO:47, or SEQ ID NO:49 are encompassed within the scope of this invention. An embodiment, for example, comprises an H3 fragment of the $V_H$ domain of antibodies chosen from at least one of PD1-17, PD1-28, PD1-33, PD1-35, and PD1-F2.

In certain embodiments, the $V_H$ and/or $V_L$ domains may be germlined, i.e., the framework regions (FRs) of these domains are mutated using conventional molecular biology techniques to match those produced by the germline cells. In other embodiments, the framework sequences remain diverged from the consensus germline sequences.

In certain embodiments, the antibodies specifically bind an epitope within the extracellular domain of human PD-1. The predicted extracellular domain consists of a sequence from about amino acid 21 to about amino acid 170 of SEQ ID NO:41 (Swissport Accession No. Q15116). In certain other embodiments, the antibodies specifically bind an epitope within the extracellular domain of mouse PD-1, with an affinity of more than $10^7$ $M^{-1}$, and preferably more than $10^8$ $M^{-1}$. The amino acid sequence of mouse PD-1 is set out in SEQ ID NO:56 (Accession No. NM_008798) and is as a whole about 60% identical to its human counterpart. In further embodiments, antibodies of the invention bind to the PD-L-binding domain of PD-1.

It is contemplated that antibodies of the invention may also bind with other proteins, including, for example, recombinant proteins comprising all or a portion of the PD-1 extracellular domain.

One of ordinary skill in the art will recognize that the antibodies of this invention may be used to detect, measure, and inhibit proteins that differ somewhat from PD-1. The antibodies are expected to retain the specificity of binding so long as the target protein comprises a sequence which is at least about 60%, 70%, 80%, 90%, 95% or more identical to any sequence of at least 100, 80, 60, 40 or 20 of contiguous amino acids in the sequence set forth SEQ ID NO:41. The percent identity is determined by standard alignment algorithms such as, for example, Basic Local Alignment Tool (BLAST) described in Altshul et al. (1990) J. Mol. Biol., 215: 403-410, the algorithm of Needleman et al. (1970) J. Mol. Biol., 48: 444-453, or the algorithm of Meyers et al. (1988) Comput. Appl. Biosci., 4: 11-17.

In addition to the sequence homology analyses, epitope mapping (see, e.g., Epitope Mapping Protocols, ed. Morris, Humana Press, 1996) and secondary and tertiary structure analyses can be carried out to identify specific 3D structures assumed by the disclosed antibodies and their complexes with antigens. Such methods include, but are not limited to, X-ray crystallography (Engstom (1974) Biochem. Exp. Biol., 11: 7-13) and computer modeling of virtual representations of the presently disclosed antibodies (Fletterick et al. (1986) Computer Graphics and Molecular Modeling, in Current Communications in Molecular Biology, Cold Spring Harbor Laboratory, Cold Spring Harbor, N.Y.).

Derivatives

This disclosure also provides a method for obtaining an antibody specific for PD-1. CDRs in such antibodies are not limited to the specific sequences of $V_H$ and $V_L$ identified in Table 1 and may include variants of these sequences that retain the ability to specifically bind PD-1. Such variants may be derived from the sequences listed in Table 1 by a skilled artisan using techniques well known in the art. For example, amino acid substitutions, deletions, or additions, can be made in the FRs and/or in the CDRs. While changes in the FRs are usually designed to improve stability and immunogenicity of the antibody, changes in the CDRs are typically designed to increase affinity of the antibody for its target. Variants of FRs also include naturally occurring immunoglobulin allotypes. Such affinity-increasing changes may be determined empirically by routine techniques that involve altering the CDR and testing the affinity antibody for its target. For example, conservative amino acid substitutions can made within any one of the disclosed CDRs. Various alterations can be made according to the methods described in Antibody Engineering, $2^{nd}$ ed., Oxford University Press, ed. Borrebaeck, 1995. These include but are not limited to nucleotide sequences that are altered by the substitution of different codons that encode a functionally equivalent amino acid residue within the sequence, thus producing a "silent" change. For example, the nonpolar amino acids include alanine, leucine, isoleucine, valine, proline, phenylalanine, tryptophan and methionine. The polar neutral amino acids include glycine, serine, threonine, cysteine, tyrosine, asparagine and glutamin. The positively charged (basic) amino acids include arginine, lysine and histidine. The negatively charged (acidic) amino acids include aspartic acid and glutamic acid. Substitutes for an amino acid within the sequence may be selected from other members of the class to which the amino acid belongs (see Table 5). Furthermore, any native residue in the polypeptide may also be substituted with alanine (see, e.g., MacLennan et al. (1998) Acta Physio. Scand. Suppl. 643:55-67; Sasaki et al. (1998) Adv. Biophys. 35:1-24).

Derivatives and analogs of antibodies of the invention can be produced by various techniques well known in the art, including recombinant and synthetic methods (Maniatis (1990) Molecular Cloning, A Laboratory Manual, 2 ed., Cold Spring Harbor Laboratory, Cold Spring Harbor, N.Y., and Bodansky et al. (1995) The Practice of Peptide Synthesis, $2^{nd}$ ed., Spring Verlag, Berlin, Germany).

TABLE 5

| Original Residues | Exemplary Substitutions | Typical Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In one embodiment, a method for making a $V_H$ domain which is an amino acid sequence variant of a $V_H$ domain of the invention comprises a step of adding, deleting, substituting, or inserting one or more amino acids in the amino acid sequence of the presently disclosed $V_H$ domain, optionally combining the $V_H$ domain thus provided with one or more $V_L$ domains, and testing the $V_H$ domain or $V_H/V_L$ combination or combinations for a specific binding to PD-1 or and, optionally, testing the ability of such antigen-binding domain to modulate PD-1 activity. The $V_L$ domain may have an amino acid sequence that is identical or is substantially as set out according to Table 1.

An analogous method can be employed in which one or more sequence variants of a $V_L$ domain disclosed herein are combined with one or more $V_H$ domains.

A further aspect of the disclosure provides a method of preparing antigen-binding fragment that specifically binds with PD-1. The method comprises:
 (a) providing a starting repertoire of nucleic acids encoding a $V_H$ domain that either includes a CDR3 to be replaced or lacks a CDR3 encoding region;
 (b) combining the repertoire with a donor nucleic acid encoding an amino acid sequence substantially as set out herein for a $V_H$ CDR3 (i.e., H3) such that the donor nucleic acid is inserted into the CDR3 region in the repertoire, so as to provide a product repertoire of nucleic acids encoding a $V_H$ domain;
 (c) expressing the nucleic acids of the product repertoire;
 (d) selecting a binding fragment specific for PD-1; and
 (e) recovering the specific binding fragment or nucleic acid encoding it.

Again, an analogous method may be employed in which a $V_L$ CDR3 (i.e., L3) of the invention is combined with a repertoire of nucleic acids encoding a $V_L$ domain, which either include a CDR3 to be replaced or lack a CDR3 encoding region. The donor nucleic acid may be selected from nucleic acids encoding an amino acid sequence substantially as set out in SEQ ID NO:17-40 or SEQ ID NO:50-55.

A sequence encoding a CDR of the invention (e.g., CDR3) may be introduced into a repertoire of variable domains lacking the respective CDR (e.g., CDR3), using recombinant DNA technology, for example, using methodology described by Marks et al. (Bio/Technology (1992) 10: 779-783). In particular, consensus primers directed at or adjacent to the 5' end of the variable domain area can be used in conjunction with consensus primers to the third framework region of human $V_H$ genes to provide a repertoire of $V_H$ variable domains lacking a CDR3. The repertoire may be combined with a CDR3 of a particular antibody. Using analogous techniques, the CDR3-derived sequences may be shuffled with repertoires of $V_H$ or $V_L$ domains lacking a CDR3, and the shuffled complete $V_H$ or $V_L$ domains combined with a cognate $V_L$ or $V_H$ domain to make the PD-1-specific antibodies of the invention. The repertoire may then be displayed in a suitable host system such as the phage display system such as described in WO92/01047 so that suitable antigen-binding fragments can be selected.

Analogous shuffling or combinatorial techniques are also disclosed by Stemmer (Nature (1994) 370: 389-391), who describes the technique in relation to a β-lactamase gene but observes that the approach may be used for the generation of antibodies.

In further embodiments, one may generate novel $V_H$ or $V_L$ regions carrying one or more sequences derived from the sequences disclosed herein using random mutagenesis of one or more selected $V_H$ and/or $V_L$ genes. One such technique, error-prone PCR, is described by Gram et al. (Proc. Nat. Acad. Sci. U.S.A. (1992) 89: 3576-3580).

Another method that may be used is to direct mutagenesis to CDRs of $V_H$ or $V_L$ genes. Such techniques are disclosed by Barbas et al. (Proc. Nat. Acad. Sci. U.S.A. (1994) 91: 3809-3813) and Schier et al. (J. Mol. Biol. (1996) 263: 551-567).

Similarly, one or more, or all three CDRs may be grafted into a repertoire of $V_H$ or $V_L$ domains, which are then screened for an antigen-binding fragment specific for PD-1.

A portion of an immunoglobulin variable domain will comprise at least one of the CDRs substantially as set out herein and, optionally, intervening framework regions from the scFv fragments as set out herein. The portion may include at least about 50% of either or both of FR1 and FR4, the 50% being the C-terminal 50% of FR1 and the N-terminal 50% of FR4. Additional residues at the N-terminal or C-terminal end of the substantial part of the variable domain may be those not normally associated with naturally occurring variable domain regions. For example, construction of antibodies by recombinant DNA techniques may result in the introduction of N- or C-terminal residues encoded by linkers introduced to facilitate cloning or other manipulation steps. Other manipulation steps include the introduction of linkers to join variable domains to further protein sequences including immunoglobulin heavy chain constant regions, other variable domains (for example, in the production of diabodies), or proteinaceous labels as discussed in further detail below.

Although the embodiments illustrated in the Examples comprise a "matching" pair of $V_H$ and $V_L$ domains, a skilled artisan will recognize that alternative embodiments may comprise antigen-binding fragments containing only a single CDR from either $V_L$ or $V_H$ domain. Either one of the single chain specific binding domains can be used to screen for complementary domains capable of forming a two-domain specific antigen-binding fragment capable of, for example, binding to PD-1. The screening may be accomplished by phage display screening methods using the so-called hierarchical dual combinatorial approach disclosed in WO92/01047, in which an individual colony containing either an H or L chain clone is used to infect a complete library of clones encoding the other chain (L or H) and the resulting two-chain specific binding domain is selected in accordance with phage display techniques as described.

Anti-PD1 antibodies described herein can be linked to another functional molecule, e.g., another peptide or protein (albumin, another antibody, etc.), toxin, radioisotope, cytotoxic or cytostatic agents. For example, the antibodies can be linked by chemical cross-linking or by recombinant methods. The antibodies may also be linked to one of a variety of nonproteinaceous polymers, e.g., polyethylene glycol, polypropylene glycol or polyoxyalkylenes, in the manner set forth in U.S. Pat. No. 4,640,835; 4,496,689; 4,301,144; 4,670,417; 4,791,192 or 4,179,337. The antibodies can be chemically modified by covalent conjugation to a polymer, for example, to increase their circulating half-life. Exemplary polymers and methods to attach them are also shown in U.S. Pat. Nos. 4,766,106; 4,179,337; 4,495,285 and 4,609,546.

The disclosed antibodies may also be altered to have a glycosylation pattern that differs from the native pattern. For example, one or more carbohydrate moieties can be deleted and/or one or more glycosylation sites added to the original antibody. Addition of glycosylation sites to the presently disclosed antibodies may be accomplished by altering the amino acid sequence to contain glycosylation site consensus sequences known in the art. Another means of increasing the number of carbohydrate moieties on the antibodies is by chemical or enzymatic coupling of glycosides to the amino acid residues of the antibody. Such methods are described in WO 87/05330 and in Aplin et al. (1981) CRC Crit. Rev. Biochem., 22: 259-306. Removal of any carbohydrate moieties from the antibodies may be accomplished chemically or enzymatically, for example, as described by Hakimuddin et al. (1987) Arch. Biochem. Biophys., 259: 52; and Edge et al. (1981) Anal. Biochem., 118: 131 and by Thotakura et al. (1987) Meth. Enzymol., 138: 350. The antibodies may also be tagged with a detectable, or functional, label.

Detectable labels include radiolabels such as $^{131}$I or $^{99}$Tc, which may also be attached to antibodies using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

Antibodies, in which CDR sequences differ only insubstantially from those set out in SEQ ID NO:2, SEQ ID NO:4, SEQ ID NO:6, SEQ ID NO:8, SEQ ID NO:10, SEQ ID NO:12, SEQ ID NO:14, SEQ ID NOs:16-40, SEQ ID NO:47, or SEQ ID NO:49 are encompassed within the scope of this invention. Typically, an amino acid is substituted by a related amino acid having similar charge, hydrophobic, or stereochemical characteristics. Such substitutions would be within the ordinary skills of an artisan. Unlike in CDRs, more substantial changes can be made in FRs without adversely affecting the binding properties of an antibody. Changes to FRs include, but are not limited to, humanizing a non-human derived or engineering certain framework residues that are important for antigen contact or for stabilizing the binding site, e.g., changing the class or subclass of the constant region, changing specific amino acid residues which might alter the effector function such as Fc receptor binding, e.g., as described in U.S. Pat. Nos. 5,624,821 and 5,648,260 and Lund et al. (1991) J. Immun. 147: 2657-2662 and Morgan et al. (1995) Immunology 86: 319-324, or changing the species from which the constant region is derived.

One of skill in the art will appreciate that the modifications described above are not all-exhaustive, and that many other modifications would be obvious to a skilled artisan in light of the teachings of the present disclosure.

Nucleic Acids, Cloning and Expression Systems

The present disclosure further provides isolated nucleic acids encoding the disclosed antibodies. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The nucleic acids provided herein comprise a coding sequence for a CDR, a $V_H$ domain, and/or a $V_L$ domain disclosed herein.

The present disclosure also provides constructs in the form of plasmids, vectors, phagemids, transcription or expression cassettes which comprise at least one nucleic acid encoding a CDR, a $V_H$ domain, and/or a $V_L$ domain disclosed here.

The disclosure further provides a host cell which comprises one or more constructs as above.

Also provided are nucleic acids encoding any CDR (H1, H2, H3, L1, L2, or L3), $V_H$ or $V_L$ domain, as well as methods of making of the encoded products. The method comprises expressing the encoded product from the encoding nucleic acid. Expression may be achieved by culturing under appropriate conditions recombinant host cells containing the nucleic acid. Following production by expression a $V_H$ or $V_L$ domain, or specific binding member may be isolated and/or purified using any suitable technique, then used as appropriate.

Antigen-binding fragments, $V_H$ and/or $V_L$ domains, and encoding nucleic acid molecules and vectors may be isolated and/or purified from their natural environment, in substantially pure or homogeneous form, or, in the case of nucleic acid, free or substantially free of nucleic acid or genes of origin other than the sequence encoding a polypeptide with the required function.

Systems for cloning and expression of a polypeptide in a variety of different host cells are well known in the art. For cells suitable for producing antibodies, see Gene Expression Systems, Academic Press, eds. Fernandez et al., 1999. Briefly, suitable host cells include bacteria, plant cells, mammalian cells, and yeast and baculovirus systems. Mammalian cell lines available in the art for expression of a heterologous polypeptide include Chinese hamster ovary cells, HeLa cells, baby hamster kidney cells, NS0 mouse myeloma cells, and many others. A common bacterial host is *E. coli*. Any protein expression system compatible with the invention may be used to produce the disclosed antibodies. Suitable expression systems include transgenic animals described in Gene Expression Systems, Academic Press, eds. Fernandez et al., 1999.

Suitable vectors can be chosen or constructed, so that they contain appropriate regulatory sequences, including promoter sequences, terminator sequences, polyadenylation sequences, enhancer sequences, marker genes and other sequences as appropriate. Vectors may be plasmids or viral, e.g., phage or phagemid, as appropriate. For further details see, for example, Sambrook et al., Molecular Cloning: A Laboratory Manual, $2^{nd}$ ed., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2 Edition, eds. Ausubel et al., John Wiley &; Sons, 1992.

A further aspect of the disclosure provides a host cell comprising a nucleic acid as disclosed here. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction of the nucleic acid into the cells may be followed by causing or allowing expression from the nucleic acid, e.g., by culturing host cells under conditions for expression of the gene.

Methods of Use

The disclosed anti-PD-1 antibodies are capable of modulating the PD-1-associated downregulation of the immune responses. In particular embodiments, the immune response is TcR/CD28-mediated. The disclosed antibodies can act as either agonists or antagonists of PD-1, depending on the method of their use. The antibodies can be used to prevent, diagnose, or treat medical disorders in mammals, especially, in humans. Antibodies of the invention can also be used for isolating PD-1 or PD-1-expressing cells. Furthermore, the antibodies can be used to treat a subject at risk of or susceptible to a disorder or having a disorder associated with aberrant PD-1 expression or function.

Antibodies of the invention can be used in methods for induction of tolerance to a specific antigen (e.g., a therapeutic protein). In one embodiment, tolerance is induced against a specific antigen by co-administration of antigen and an anti-PD-1 antibody of the invention. For example, patients that received Factor VIII frequently generate antibodies to this protein; co-administration of an anti-PD-1 antibody of the invention in combination with recombinant Factor VIII is expected to result in the downregulation of immune responses to this clotting factor.

Antibodies of the invention can be used in circumstances where a reduction in the level of immune response may be desirable, for example, in certain types of allergy or allergic reactions (e.g., by inhibition of IgE production), autoimmune diseases (e.g., rheumatoid arthritis, type I diabetes mellitus, multiple sclerosis, inflammatory bowel disease, Crohn's disease, and systemic lupus erythematosis), tissue, skin and organ transplant rejection and graft-versus-host disease (GVHD).

When diminished immune response is desirable, the anti-PD-1 antibodies of the invention may be used as agonists to PD-1 in order to enhance the PD-1-associated attenuation of the immune response. In these embodiments, co-presentation and physical proximity between positive (i.e., mediated by an antigen receptor, e.g., TcR or BcR) and negative (i.e., PD-1) signals are required. The preferred distance is less than or comparable to the size of a naturally occurring antigen-presenting cell, i.e., less than about 100 μm; more preferably, less than about 50 μm; and most preferably, less than about 20 μm.

In some embodiments, the positive (activating) and the negative (inhibiting) signals are provided by a ligand or antibodies immobilized on solid support matrix, or a carrier. In various embodiments, the solid support matrix may be composed of polymer such as activated agarose, dextran, cellulose, polyvinylidene fluoride (PVDF). Alternatively, the solid support matrix may be based on silica or plastic polymers, e.g., as nylon, dacron, polystyrene, polyacrylates, polyvinyls, teflons, etc.

The matrix can be implanted into the spleen of a patient. Alternatively, the matrix may be used for the ex vivo incubation of T cells obtained from a patient, which are then separated and implanted back into the patient. The matrix may also be made from a biodegradable material such polyglycolic acid, polyhydroxyalkanoate, collagen or gelatin so that they can be injected into the patient's peritoneal cavity, and dissolve after some time following the injection. The carrier can be shaped to mimic a cell (e.g., bead or micro sphere).

In some embodiments, the positive signal is delivered by a T-cell-activating anti-CD3 antibody, which binds TcR. Activating anti-CD3 antibodies are known in the art (see, for example, U.S. Pat. Nos. 6,405,696 and 5,316,763). The ratio between the activating TcR signal and negative PD-1 signal is determined experimentally using conventional procedures known in the art or as described in Examples 8, 9 and 10.

Under certain circumstances, it may be desirable to elicit or enhance a patient's immune response in order to treat an immune disorder or cancer. The disorders being treated or prevented by the disclosed methods include but are not limited to infections with microbes (e.g., bacteria), viruses (e.g., systemic viral infections such as influenza, viral skin diseases such as herpes or shingles), or parasites; and cancer (e.g., melanoma and prostate cancers).

Stimulation of T cell activation with anti-PD-1 antibodies enhances T-T cell responses. In such cases, antibodies act as antagonists of PD-1. Thus, in some embodiments, the antibodies can be used to inhibit or reduce the downregulatory activity associated with PD-1, i.e., the activity associated with a downregulation of TcR/CD28-mediated immune response. In these embodiments, the antibodies are not coupled to a positive signal such as the TcR-mediated stimulation, e.g., the antibodies are in their soluble, support-unbound, form. As demonstrated in the Examples, a blockade of PD-1/PD-L interaction with antagonizing anti-PD-1 antibodies leads to enhanced T cell proliferative responses, consistent with a downregulatory role for the PD-1 pathway in T-T interactions. In various embodiments, the antibodies inhibit binding of PD-L to PD-1 with an $IC_{50}$ of less than 10 nM, and more preferably less than 5 nM, and most preferably less than 1 nM. Inhibition of PD-L binding can be measured as described in Example 6 or using techniques known in the art.

The antibodies or antibody compositions of the present invention are administered in therapeutically effective amounts. Generally, a therapeutically effective amount may vary with the subject's age, condition, and sex, as well as the severity of the medical condition of the subject. A therapeutically effective amount of antibody ranges from about 0.001 to about 30 mg/kg body weight, preferably from about 0.01 to about 25 mg/kg body weight, from about 0.1 to about 20 mg/kg body weight, or from about 1 to about 10 mg/kg. The dosage may be adjusted, as necessary, to suit observed effects of the treatment. The appropriate dose is chosen based on clinical indications by a treating physician.

The antibodies may be given as a bolus dose, to maximize the circulating levels of antibodies for the greatest length of time after the dose. Continuous infusion may also be used after the bolus dose.

Immune cells (e.g., activated T cells, B cells, or monocytes) can also be isolated from a patient and incubated ex vivo with antibodies of the invention. In some embodiments, immune responses can be inhibited by removing immune cells from a subject, contacting the immune cells in vitro with an anti-PD-1 antibody of the invention concomitantly with activation of the immune cells (e.g., by antibodies to the TcR and/or BcR antigen receptor). In such embodiments, the anti-PD-1 antibody should be used in a multivalent form such that PD-1 molecules on the surface of an immune cell become "crosslinked" upon binding to such antibodies. For example, the anti-PD-1 antibodies can be bound to solid support, such as beads, or crosslinked via a secondary antibody. The immune cells may be then isolated using methods known in the art and reimplanted into the patient.

In another aspect, the antibodies of the invention can be used as a targeting agent for delivery of another therapeutic or a cytotoxic agent (e.g., a toxin) to a cell expressing PD-1. The method includes administering an anti-PD-1 antibody coupled to a therapeutic or a cytotoxic agent or under conditions that allow binding of the antibody to PD-1.

The antibodies of the invention may also be used to detect the presence of PD-1 in biological samples. The amount of PD-1 detected may be correlated with the expression level of PD-1, which, in turn, is correlated with the activation status of immune cells (e.g., activated T cells, B cells, and monocytes) in the subject.

Detection methods that employ antibodies are well known in the art and include, for example, ELISA, radioimmunoassay, immunoblot, Western blot, immunofluorescence, immunoprecipitation. The antibodies may be provided in a diagnostic kit that incorporates one or more of these techniques to detect PD-1. Such a kit may contain other components, packaging, instructions, or other material to aid the detection of the protein.

Where the antibodies are intended for diagnostic purposes, it may be desirable to modify them, for example, with a ligand group (such as biotin) or a detectable marker group (such as a fluorescent group, a radioisotope or an enzyme). If desired, the antibodies of the invention may be labeled using conventional techniques. Suitable detectable labels include, for example, fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. For detection, suitable binding partners include, but are not limited to, biotin and avidin or streptavidin, IgG and protein A, and the numerous receptor-ligand couples known in the art. Other permutations and possibilities will be readily apparent to those of ordinary skill in the art, and are considered as equivalents within the scope of the instant invention.

Antibodies of the invention can be used in screening methods to identify inhibitors of the PD-1 pathway effective as therapeutics. In such a screening assay, a first binding mixture is formed by combining PD-1 and an antibody of the invention; and the amount of binding in the first binding mixture $(M_0)$ is measured. A second binding mixture is also formed by combining PD-1, the antibody, and the compound or agent to be screened, and the amount of binding in the second binding mixture $(M_1)$ is measured. A compound to be tested may be another anti-PD-1 antibody, as illustrated in the Examples. The amounts of binding in the first and second binding mixtures are then compared, for example, by calculating the $M_1/M_0$ ratio. The compound or agent is considered to be capable of modulating a PD-1-associated downregulation of immune responses if a decrease in binding in the second binding mixture as compared to the first binding mixture is observed. The formulation and optimization of binding mixtures is within the level of skill in the art, such binding mixtures may also contain buffers and salts necessary to enhance or to optimize binding, and additional control assays may be included in the screening assay of the invention. Compounds found to reduce the PD-1-antibody binding by at least about 10% (i.e., $M_1/M_0<0.9$), preferably greater than about 30% may thus be identified and then, if desired, secondarily screened for the capacity to ameliorate a disorder in other assays or animal models as described below. The strength of the binding between PD-1 and an antibody can be measured using, for example, an enzyme-linked immunoadsorption assay (ELISA), radio-immunoassay (RIA), surface plasmon resonance-based technology (e.g., Biacore), all of which are techniques well known in the art.

The compound may then be tested in vitro as described in the Examples or in an animal model (see, generally, Immunologic Defects in Laboratory Animals, eds. Gershwin et al., Plenum Press, 1981), for example, such as the following: the SWR X NZB (SNF1) transgenic mouse model (Uner et al. (1998) J. Autoimmune. 11(3): 233-240), the KRN transgenic mouse (K/BxN) model (Ji et al. (1999) Immunol. Rev. 169: 139); NZB X NZW (B/W) mice, a model for SLE (Riemekasten et al. (2001) Arthritis Rheum., 44(10): 2435-2445); experimental autoimmune encephalitis (EAE) in mouse, a model for multiple sclerosis (Tuohy et al. (1988) J. Immunol. 141: 1126-1130, Sobel et al. (1984) J. Immunol. 132: 2393-2401, and Traugott, Cell Immunol. (1989) 119: 114-129); the NOD mouse model of diabetes (Baxter et al. (1991) Autoimmunity, 9(1): 61-67), etc.).

Preliminary doses as, for example, determined according to animal tests, and the scaling of dosages for human administration is performed according to art-accepted practices. Toxicity and therapeutic efficacy can be determined by standard pharmaceutical procedures in cell cultures or experimental animals. The data obtained from the cell culture assays or animal studies can be used in formulating a range of dosage for use in humans. Therapeutically effective dosages achieved in one animal model can be converted for use in another animal, including humans, using conversion factors known in the art (see, e.g., Freireich et al. (1966) Cancer Chemother. Reports, 50(4): 219-244).

Pharmaceutical Compositions and Methods of Administration

The disclosure provides compositions comprising anti-PD-1 antibodies. Such compositions may be suitable for pharmaceutical use and administration to patients. The compositions typically comprise one or more antibodies of the present invention and a pharmaceutically acceptable excipient. The phrase "pharmaceutically acceptable excipient" includes any and all solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. The administration may, for example, be intravenous, intraperitoneal, intramuscular, intracavity, subcutaneous or transdermal. It may also be possible to obtain compositions which may be topically or orally administered, or which may be capable of transmission across mucous membranes.

Solutions or suspensions used for intradermal or subcutaneous application typically include one or more of the following components: a sterile diluent such as water for injection, saline solution, fixed oils, polyethylene glycols, glycerin, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and/or by the use of surfactants. Prolonged absorption of the injectable compositions can be brought about by including in the composition an agent which delays absorption, for example, aluminum monostearate, and gelatin.

Oral compositions generally include an inert diluent or an edible carrier. They can be enclosed in gelatin capsules or compressed into tablets. For oral administration, the antibodies can be combined with excipients and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, detergents, bile salts, and fusidic acid derivatives. Transmucosal administration may be accomplished, for example, through the use of lozenges, nasal sprays, inhalers or suppositories. For example, in case of antibodies that comprise the Fc portion, compositions may be capable of transmission across mucous membranes in intestine, mouth, or lungs (e.g., via the FcRn receptor-mediated pathway as described in U.S. Pat. No. 6,030,613). For transdermal administration, the active compounds may be formulated into ointments, salves, gels, or creams as generally known in the art. For administration by inhalation, the antibodies may be delivered in the form of an aerosol spray from pressured container or dispenser, which contains a suitable propellant, e.g., a gas such as carbon dioxide or a nebulizer.

In certain embodiments, the presently disclosed antibodies are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. Liposomal suspensions containing the presently disclosed antibodies can also be used as pharmaceutically acceptable carriers. These can be prepared according to methods known to those skilled in the art, for example, as described in U.S. Pat. No. 4,522,811.

It may be advantageous to formulate oral or parenteral compositions in a dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of the composition of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

For any composition used in the present invention, the therapeutically effective dose can be estimated initially from cell culture assays. Examples of suitable bioassays include DNA replication assays, cytokine release assays, transcription-based assays, PD-1/PD-L1 binding assays, creatine kinase assays, assays based on the differentiation of pre-adipocytes, assays based on glucose uptake in adipocytes, immunological assays other assays as, for example, described in the Examples. The data obtained from the cell culture assays and animal studies can be used in formulating a range of dosage for use in humans. A dose may be formulated in animal models to achieve a circulating plasma concentration range that includes the $IC_{50}$ (i.e., the concentration of the antibody which achieves a half-maximal inhibition of symptoms). Circulating levels in plasma may be measured, for example, by high performance liquid chromatography. The effects of any particular dosage can be monitored by a suitable bioassay. The dosage lies preferably within a range of circulating concentrations with little or no toxicity. The dosage may vary depending upon the dosage form employed and the route of administration utilized.

The following Examples do not in any way limit the scope of the invention. One of ordinary skill in the art will recognize the numerous modifications and variations that may be performed without altering the spirit or scope of the present invention. Such modifications and variations are encompassed within the scope of the invention. The entire contents of all references, patents, and published patent applications cited throughout this application are herein incorporated by reference.

EXAMPLES

Example 1

Selection of PD-1 Binding ScFv's

An scFv phagemid library, which is an expanded version of the $1.38 \times 10^{10}$ library described by Vaughan et al. (Nature Biotech. (1996) 14: 309-314) was used to select antibodies specific for human PD-1. Soluble PD-1 fusion protein (at 20 µg/ml in phosphate buffered saline (PBS)) or control fusion protein (at 50 µg/ml in PBS) was coated onto wells of a microtiter plate overnight at 4° C. Wells were washed in PBS and blocked for 1 hour at 37° C. in MPBS (3% milk powder in PBS). Purified phage (1012 transducing units (tu)) was blocked for 1 hour in a final volume of 100 µl of 3% MPBS. Blocked phage was added to blocked control fusion protein wells and incubated for 1 hour. The blocked and deselected phage were then transferred to the blocked wells coated with the PD-1 fusion protein and were incubated for an additional hour. Wells were washed 5 times with PBST (PBS containing 0.1% v/v Tween 20), then 5 times with PBS. Bound phage particles were eluted and used to infect 10 ml exponentially growing E. coli TG1. Infected cells were grown in 2TY broth for 1 hour at 37° C., then spread onto 2TYAG plates and incubated overnight at 30° C. Colonies were scraped off the plates into 10 ml 2TY broth and 15% glycerol added for storage at −70° C.

Glycerol stock cultures from the first round of panning selection were superinfected with helper phage and rescued to give scFv antibody-expressing phage particles for the second round of panning. A total of two rounds of panning were carried out in this way for isolation of PD1-17, except in the second round of panning 20 µg/ml of control protein were used for deselection. Clones PD1-28, PD1-33, and PD1-35 were selected following three rounds of selection. Deselection in the second and third rounds was carried out using 10 µg/ml control fusion protein.

Antibodies to murine PD-1 were selected by soluble selection using biotinylated murine PD-1 fusion protein at a final concentration of 100 nM. An scFv phagemid library, as described above, was used. Purified scFv phage ($10^{12}$ tu) in 1 ml 3% MPBS were blocked for 30 minutes, then biotinylated antigen was added and incubated at room temperature for 1 hour. Phage/antigen was added to 250 µl of Dynal M280 Streptavidin magnetic beads that had been blocked for 1 hour at 37° C. in 1 ml of 3% MPBS and incubated for a further 15 minutes at room temperature. Beads were captured using a magnetic rack and washed 4 times in 1 ml of 3% MPBS/0.1% (v/v) Tween 20 followed by 3 washes in PBS. After the last PBS wash, beads were resuspended in 100 µl PBS and used to infect 5 ml exponentially growing E. coli TG-1 cells. Infected cells were incubated for 1 hour at 37° C. (30 minutes stationary, 30 minutes shaking at 250 rpm), then spread on 2TYAG plates and incubated overnight at 30° C. Output colonies were scraped off the plates and phage rescued as described above. A second round of soluble selection was carried out as described above.

Example 2

Specificity of Antibodies for PD-1 by a Phage ELISA

To determine the specificity of antibodies for PD-1, a phage ELISA was performed against PD-1 fusion protein and control proteins. Individual E. coli colonies from selection outputs were picked into 96 well plates containing 100 µl of 2TYAG medium per well. M13K07 helper phage was added to a multiplicity of infection (moi) of 10 to the exponentially growing culture and the plates incubated an additional 1 hour at 37° C. Plates were centrifuged in a benchtop centrifuge at 2000 rpm for 10 minutes. The supernatant was removed and cell pellets were resuspended in 100 µl 2TYAK and incubated at 30° C. overnight with shaking. The next day, plates were centrifuged at 2000 rpm for 10 minutes and phage-containing supernatant from each well was transferred to a fresh 96 well plate. Phage samples were blocked in a final concentration of 3% MPBS prior to ELISA.

Human or mouse PD-1 fusion protein and control fusion and non-fusion proteins were coated overnight at 4° C. onto 96-well microtiter plates at 0.5-2.5 µg/ml in PBS. After coating, the solutions were removed from the wells, and the plates blocked for 1 hour in 3% MPBS. Plates were rinsed with PBS and then 50 µl of pre-blocked phage were added to each well. The plates were incubated for 1 hour and then washed 3 times with PBST followed by 3 washes with PBS. To each well, 50 µl of a 1:5000 dilution of anti-M13-HRP conjugate (Pharmacia, Peapack, N.J.) was added, and the plates incubated for 40-60 minutes. Each plate was washed three times with PBST then 3 times with PBS. Fifty µl of TMB substrate was added to each well, and the samples were incubated until color development. The reaction was stopped by the addition of 25 µl of 0.5 M $H_2SO_4$. The signal generated was measured by reading the absorbance at 450 nm using a microtiter plate reader. Clones showing specific binding to PD-1 fusion protein but not to control fusion proteins were thus identified and confirmed.

Figure 1B:
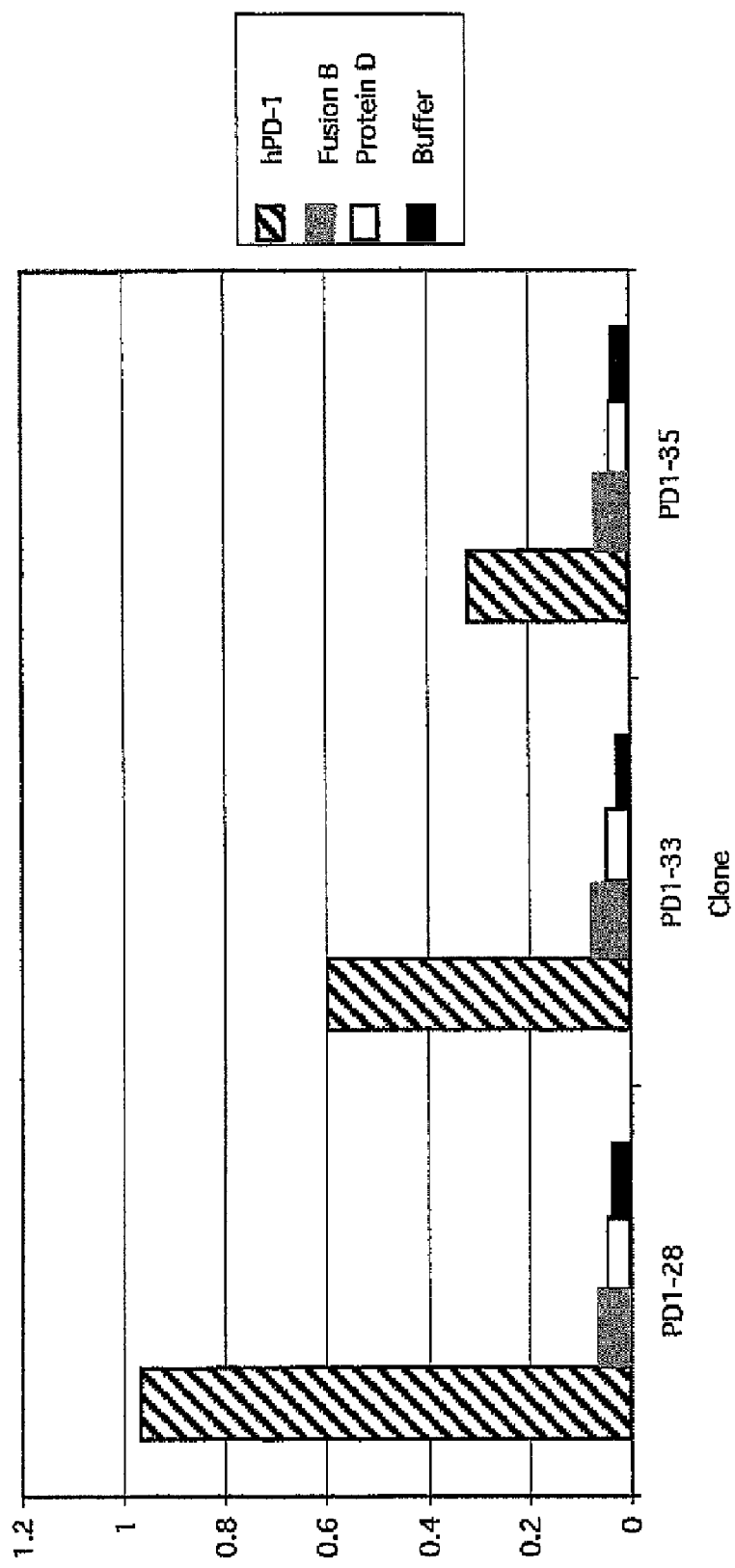

Specificity data for the PD1-17 scFv is shown in FIG. 1A. Reactivity of PD1-28, PD1-33, and PD1-35 scFv's with human PD-1 is shown in FIG. 1B (an $IgG_1$ control did not bind PD-1).

Example 3

Identification of Antibody Clones

PD-1-binding scFv *E. coli* clones were streaked out onto 2TYAG plates and incubated overnight at 30° C. Colonies from these plates were sequenced using pCANTAB6 vector sequence oligos to amplify the $V_H$ and $V_L$ regions from the scFv clone. Unique PD-1 binding clones were assayed for neutralization of PD-L1 binding to PD-1 as described in Example 4. Sequence differences between scFv and IgG formats are due to changes introduced by PCR primers during the conversion from scFv to IgG.

Example 4

Biochemical Binding Inhibition Assay and Screen

ScFv production was induced by addition of 1 mM IPTG to exponentially growing cultures and incubation overnight at 30° C. Crude scFv-containing periplasmic extracts were obtained by subjecting the bacterial pellets from the overnight induction to osmotic shock. Pellets were resuspended in 20% (w/v) sucrose, 50 mM Tris-HCl, pH 7.5, 1 mM EDTA and cooled on ice for 30 minutes. Cellular debris was removed by centrifugation, and the scFv was purified by chromatography and buffer-exchanged into PBS. Purified scFv's (PD1-17, PD1-28, PD1-33, and PD1-35) were tested for the ability to inhibit the binding of biotinylated human PD-L1 fusion protein to human PD-1 fusion protein immobilized on plastic in a 96 well microtiter plate assay. Binding of biotinylated PD-L1 fusion protein was detected with AMDEX-alkaline phosphatase, and the signal generated was measured by reading the absorbance at 405 nm using a microtiter plate reader. Data was expressed as a percentage of the total binding and a titration of scFv concentrations was tested to establish clone potency as calculated $IC_{50}$ values. Clone potency data for the scFv and IgG antibodies is shown in Table 5.

PD1-F2 scFv was produced and purified as described above. Cells expressing murine PD-1 were added at $10^5$ cells/well in a final volume of 100 µl to a poly-D-lysine-coated 96 well microtiter plate. Cells were centrifuged and washed twice in PBS, then blocked with 300 µl 1% BSA in PBS for 1 hour at room temperature. Blocked cells were washed three times in PBST, prior to addition of 25, µl/well of assay buffer (0.05% BSA, 0.05% Tween 20 in Dulbecco's PBS) or sample, followed by 25 µl of biotinylated murine PD-L1 fusion protein at 300 ng/ml. Binding of biotinylated PD-L1 fusion protein was detected with Amdex alkaline phosphatase and signals read as described above. Potencies of PD1-F2 scFv and IgG are shown in Table 6.

TABLE 6

Potency of Anti-PD-1 ScFv and IgG Antibodies

| Clone | ScFv $IC_{50}$ (nM) | IgG $IC_{50}$ (nM) |
|---|---|---|
| PD1-17 | 726 | 2.5 |
| PD1-28 | 560 | 1.4 |
| PD1-33 | 74 | 1.8 |
| PD1-35 | 85 | 2.3 |
| PD1-F2 | 28 | 1.0 |

Example 5

Conversion of ScFv to IgG

Heavy and light chain V regions from scFv clones were amplified by PCR using clone-specific primers. PCR products were digested with appropriate restriction enzymes and subcloned into vectors containing human $IgG_1$ heavy chain constant domain (Takahashi et al. (1982) Cell 29, 671) or vectors containing human lambda or kappa light chain constant domains (Hieter et al. (1982) Nature 294, 536). Based on the germlines of the $V_H$ and $V_L$ segments, it was determined whether kappa or lambda light chain constant domains were used for conversion (Table 7).

TABLE 7

Germlines of $V_H$ and $V_L$ Regions of PD-1 Antibody Clones

| Clone | $V_H$ germline | $V_L$ germline |
|---|---|---|
| PD1-17 | DP-70 | DPL-8 |
| PD1-28 | DP-14 | DPL-23 |
| PD1-33 | DP-7 | DPL-11 |
| PD1-35 | DP-65 | DPL-2 |
| PD1-F2 | DP-47 | L12 (κ) |

The insertion of V region domains into plasmids was verified by sequencing of plasmid DNA from individual *E. coli* colonies. Plasmids were prepared from *E. coli* cultures by standard techniques and heavy and light chain constructs cotransfected into eukaryotic cells using standard techniques. Secreted IgG was purified using Protein A Sepharose (Pharmacia) and buffer-exchanged into PBS.

The binding affinity of the anti-mouse PD1 antibody PD1-F2 was determined with a Surface Plasmon Resonance (SPR)

system (BIAcore 3000) (Biacore, Piscataway, N.J.) using murine PD-1 fusion immobilized on a CM5 sensor chip. The concentration of PD1-F2 in the flow cell ranged from 7.81 to 125 nM, while the concentration of the anti-mouse PD1 antibody J43 (eBioscience, San Diego, Calif.) ranged from 25 nM to 500 nM. The equilibrium constant $K_D$ for PD1-F2 is $6.7 \times 10^{-9}$ M ($K_A = 1.5 \times 10^8$ M$^{-1}$), whereas $K_D$ for J43 is $3.8 \times 10^{-7}$ M ($K_A = 2.6 \times 10^6$ M$^{-1}$).

Figure 2A:
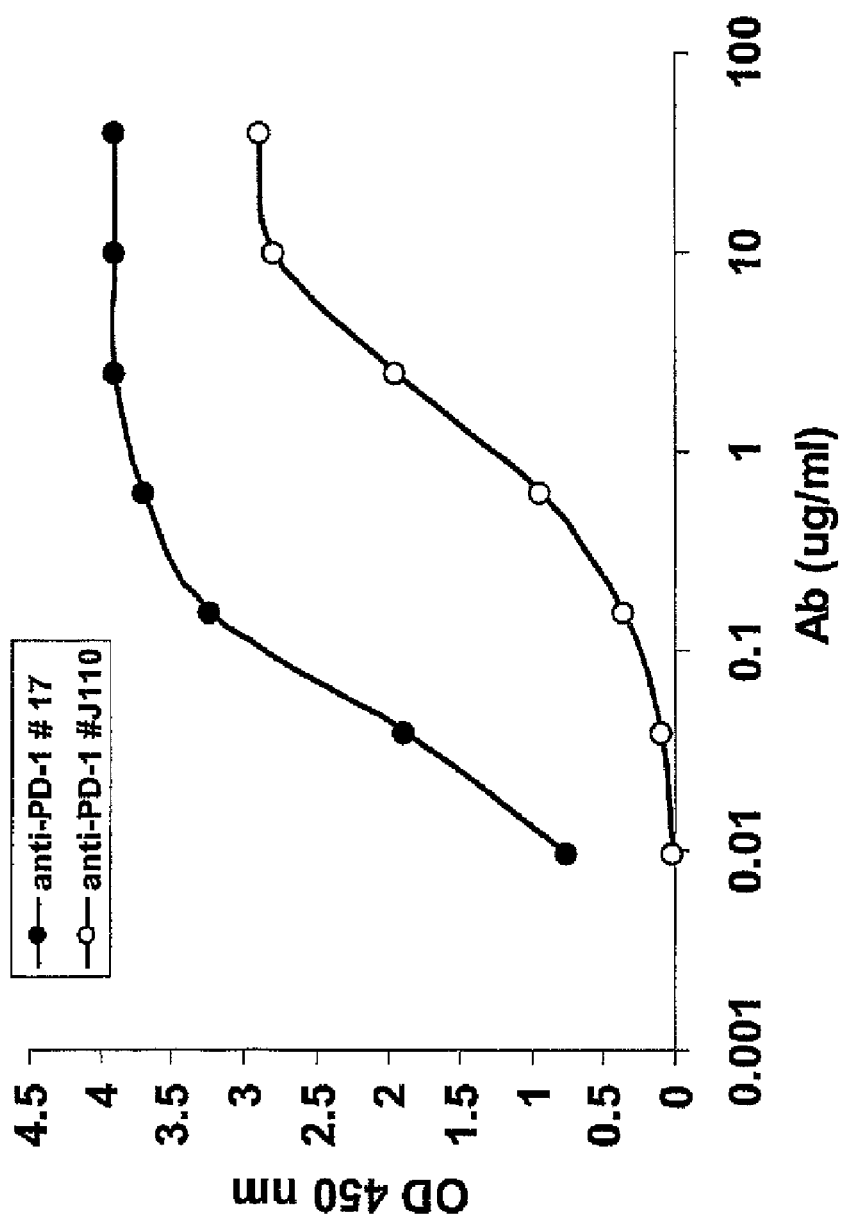
FIGS. 2A-2C show reactivity of IgG-converted antibodies with human or mouse PD-1 as determined by ELISA.
Figure 2B:
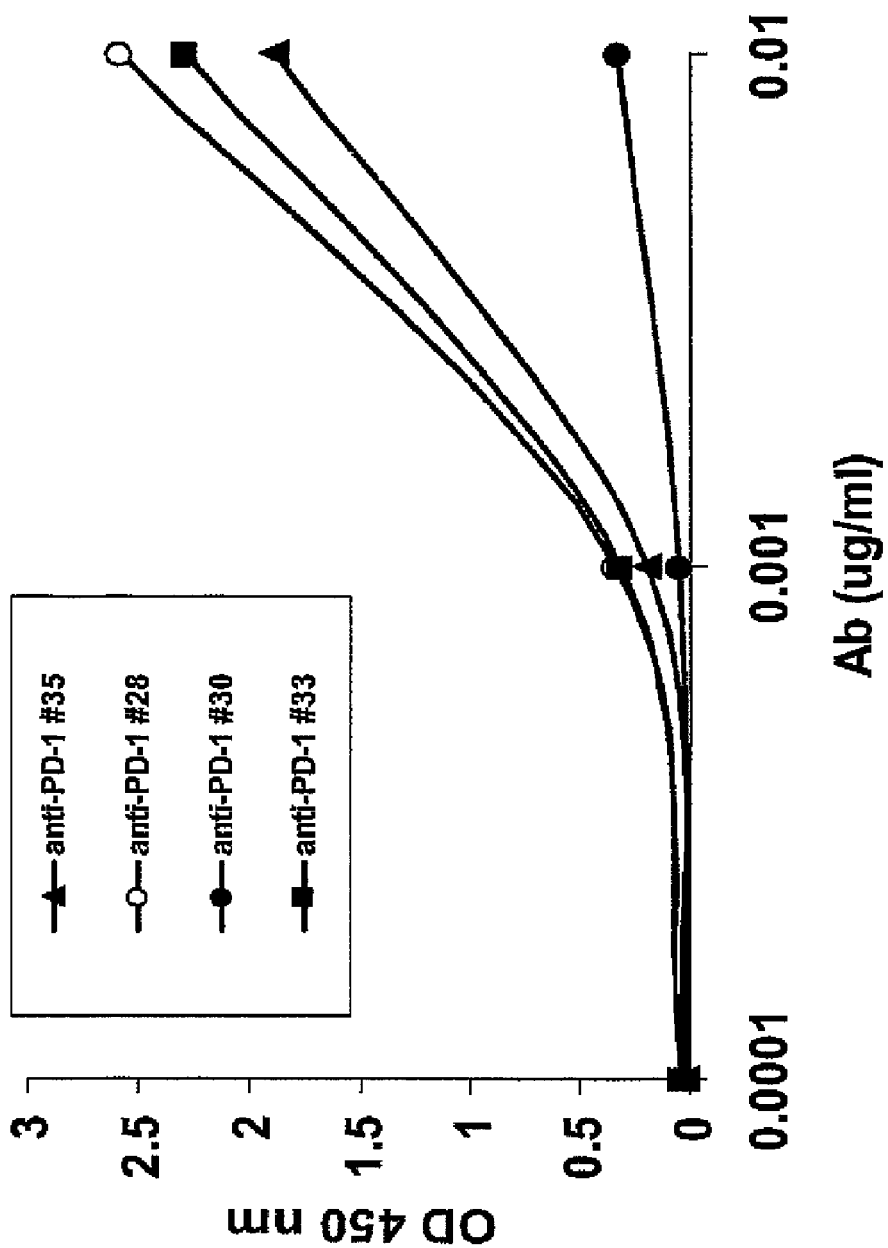
Figure 2C:
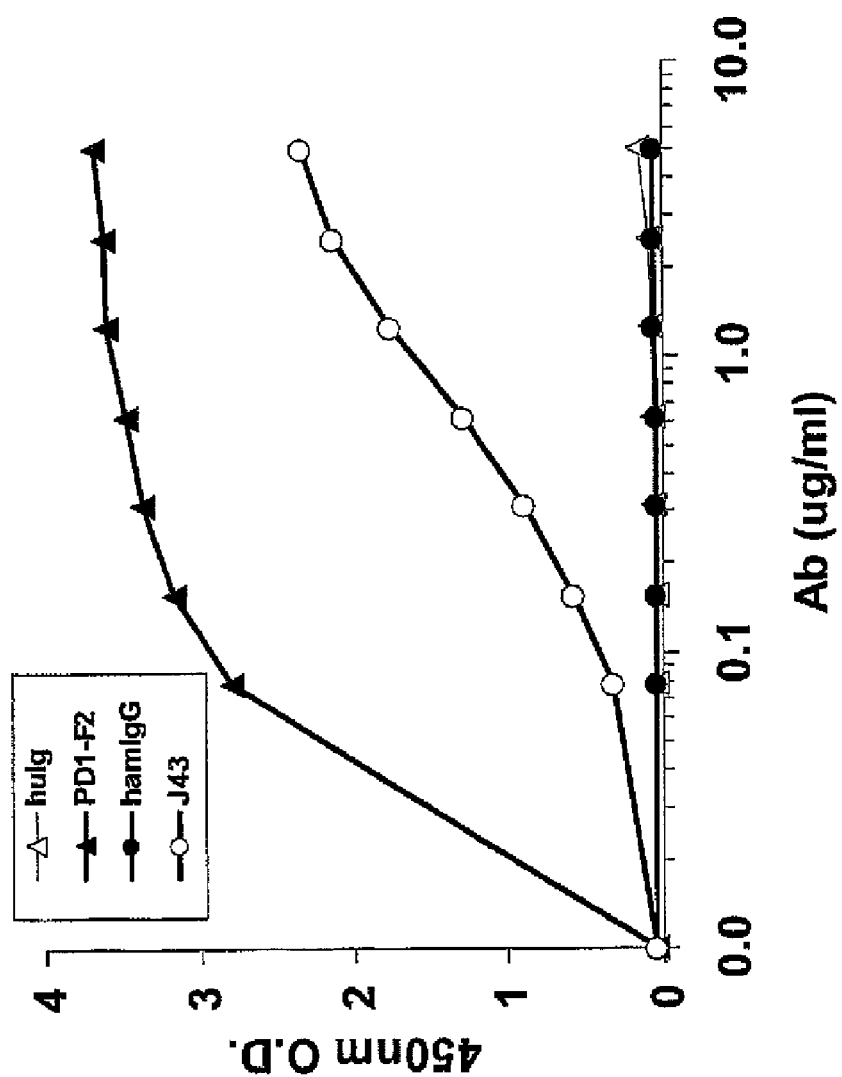

The ability of anti-PD-1 IgG's to bind human or murine PD-1 was determined as follows. ELISA plates were incubated with 2.5 µg/ml human PD-1/IgG chimera overnight. Plates were washed with PBS/1% BSA and incubated with serial dilutions of a test antibody for 2 hours at room temperature (RT). After washing, saturating concentrations of HRP-conjugated goat anti-human antibody or HRP-conjugated rabbit anti-murine antibody were added, and the samples were incubated for 1 hour at RT. Unbound goat and rabbit antibodies were washed using PBS/1% BSA. The assay was developed using TBM. Results were expressed as OD 405 absorbency values and are presented in FIGS. 2A-2C. Murine anti-human PD-1 antibody J110 is commercially available (eBioscience, San Diego, Calif.) and was included for comparison.

Example 6

Selected PD-1 Antibodies Inhibit Binding of PD-L1 to PD-1

Inhibition assays were performed to assess the ability of the antibodies to block binding of PD-L1 to PD-1. ELISA was performed as described in Example 2 with modifications. After incubation with a primary, anti-PD-1 antibody for 2 hours at RT, a fixed concentration (1 µg/ml) of biotin-conjugated PD-L1-Ig was added, and the samples were further incubated for 1 hour at RT. After washing, saturating concentrations of avidin-HRP were added, and incubated for 1 hour at RT. Unbound avidin-HRP was washed using PBS/1% BSA. The assay was developed using TMB.

Figure 3:
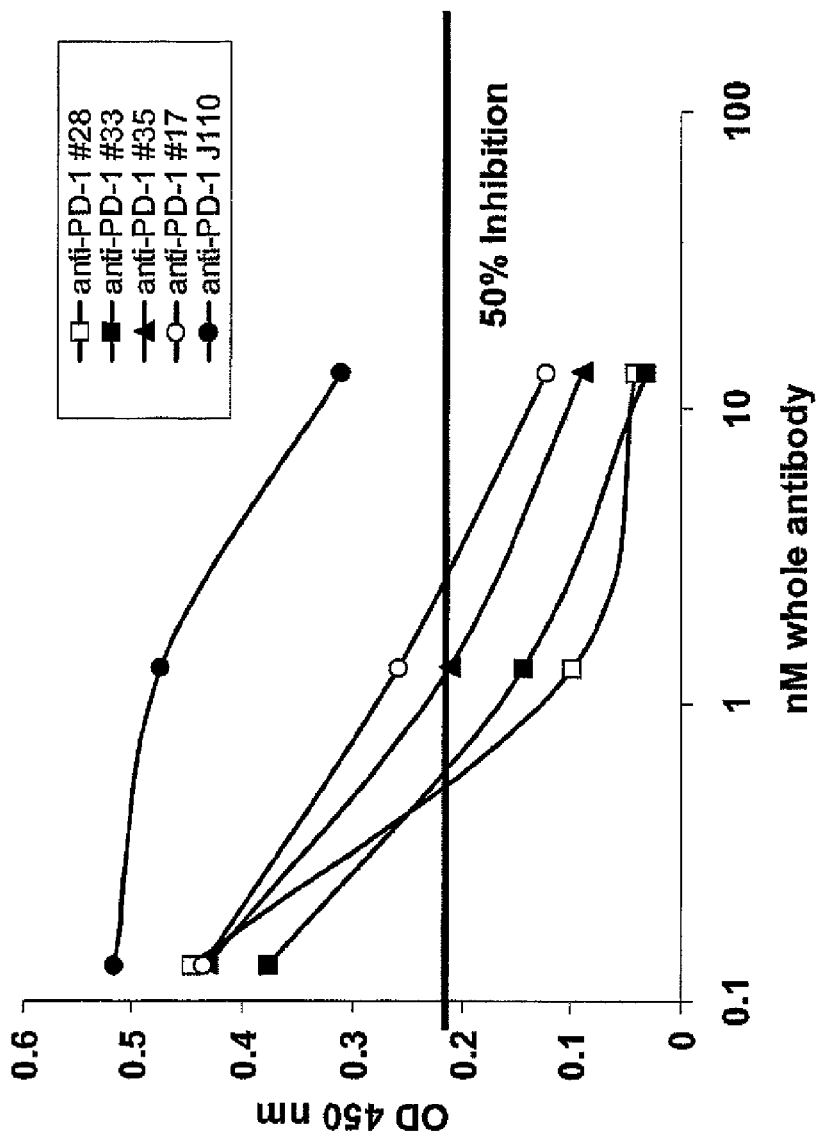
FIG. 3 shows results of an ELISA demonstrating that selected PD-1 antibodies inhibit binding of PD-L1 to PD-1.

Results were compared to those obtained with J110 as shown in FIG. 3. Anti-human PD-1 antibodies J110 and PD1-30 did not inhibit the binding of PD-L1 to PD-1. Anti-human antibodies PD1-17, PD1-28, PD1-33 and PD1-35 and anti-mouse antibody PD1-F2 block PD-1/PD-L1 interaction.

Example 7

PD-1 Antibodies Recognize Distinct Sites on PD-1

Inhibition assays were performed to map sites recognize by the various human anti-human PD-1 antibodies. ELISA was performed as described in Example 6 with minor modifications. After incubation with primary antibody for 2 hours at RT, a fixed concentration (0.25 µg/ml) of biotin-conjugated anti-PD-1 antibody J110 was added, and the samples were further incubated for 1 hour at RT. After washing, saturating concentrations of avidin-HRP were added, and incubated for 1 hour at RT. Unbound avidin-HRP was washed using PBS/1% BSA. The assay was developed using TMB.

Figure 4:
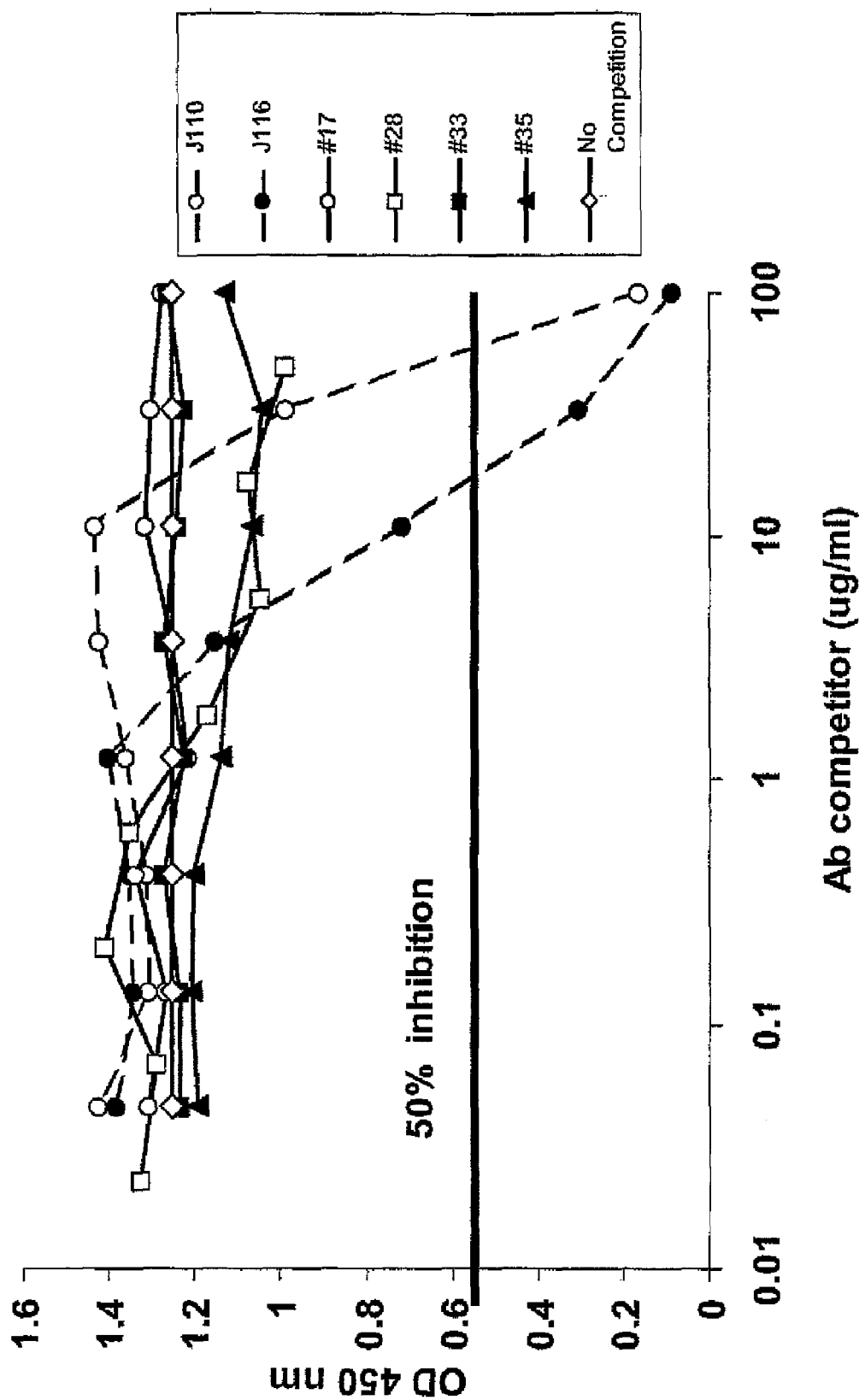
FIG. 4 shows results of an ELISA demonstrating that immunomodulatory PD-1 antibodies bind to distinct sites on PD-1 as determined by cross-blocking ELISA assays.

As shown in FIG. 4, binding of anti-human PD-1 antibodies (J110, J116, PD1-17, PD1-28, PD1-33, and PD1-35) defines at least two distinct sites on PD-1. Cross-blocking results show that J110 and J116, bind to identical or overlapping sites while PD1-17, 28, 33, and 35 bind to another distinct site. Binding of J116 or J110 to PD-1 blocks the binding of J110. In contrast, binding of PD1-17, PD1-28, PD1-33, and PD1-35 do not block binding of J110. This suggests that the tested anti-PD-1 antibodies bind to at least two distinct epitopes: one recognized by J110 and J116, and the other one recognized by PD1-17, PD1-28, PD1-33 and PD1-35.

Example 8

PD-1 Engagement Results in Decreased T Cell Responses

CD4+ T cells ($5 \times 10^4$ cells/well) were stimulated with tosyl-beads (Dynal, Great Neck, N.Y.) coated with anti-hCD3+/−PD-L1-Fc or anti-PD-1 (PD1-17 or J110). Concentration of fusion protein or antibody titer was as indicated in the X-axis of FIG. 5. After 72 hours, proliferation was determined by $^3$H-thymidine incorporation. Incorporated radioactivity was determined using a LKB 1205 plate reader.

Figure 5:
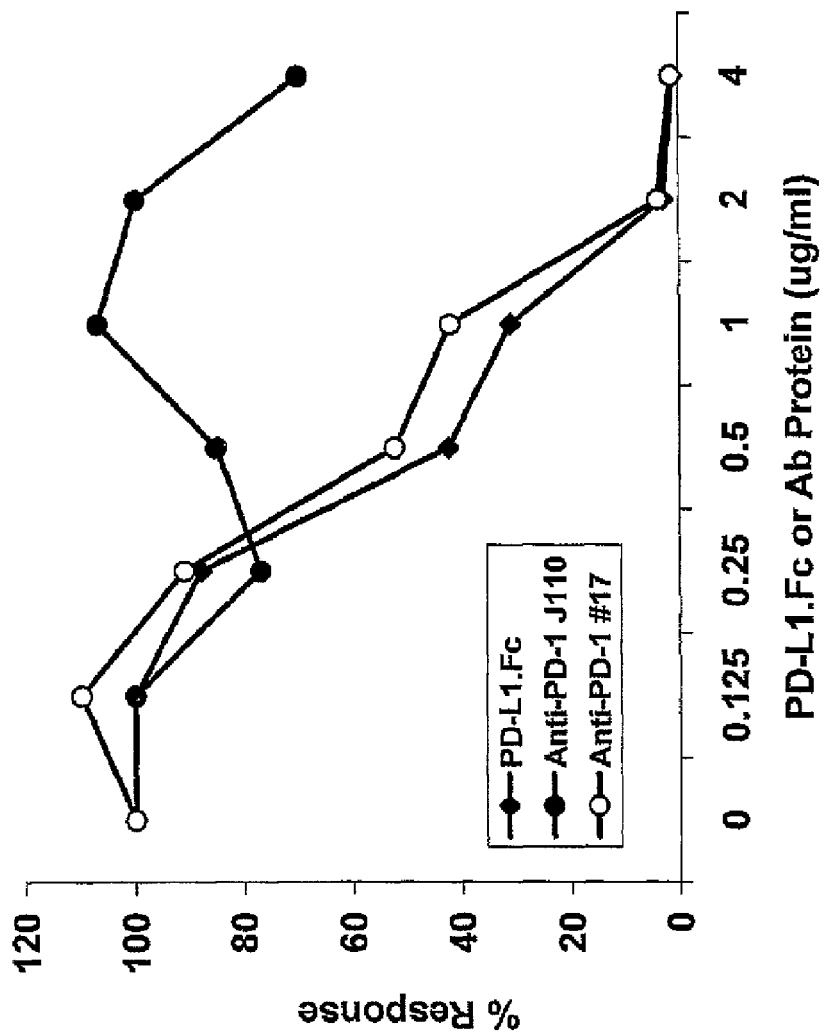
FIG. 5 shows results of T-cell proliferation assays demonstrating that co-engagement by TcR and anti-PD-1 antibody PD1-17 or PD-L1.Fc reduces proliferation. Co-engagement by TcR and anti-PD-1 J 110 has no effect on proliferation.

As shown in FIG. 5, PD-1 engagement by anti-PD-1 antibody PD1-17 or PD-L1.Fc caused a decrease in T cell proliferation. Thus, PD1-17 can mimic PD-1 ligands and delivered an inhibitory signal. As discussed below (Example 9), this inhibitory signal results in decreased T cell proliferation and IL-2 production. Antibodies PD1-28, PD1-33, and PD1-35 have the same effect as PD1-17. The effect is dose-dependent, as activation of cells in the presence of increasing concentrations of PD1-17 or PD-L1.Fc results in decreased T cell proliferation. The control anti-PD-1 antibodies, J110 (FIG. 5) or J116 (data not shown), do not inhibit T cell responses and increasing the concentration of J110 has minimal effect on T cell proliferation. For comparison, values are represented as percentage of the anti-CD3 response. "100%" represents CPMs obtained when cells were activated with anti-CD3/murine IgG-coated microspheres. Altogether these results indicate that some but not all antibodies that recognize PD-1 can act as agonists of the PD-1 pathway.

Further experiments were performed to address whether PD-1 downregulation of T cell responses required coordinate TcR/PD-1 engagement on a single (CIS) or a separate (TRANS) cell surfaces. Two sets of microspheres were prepared: one set contained anti-CD3 and PD-L1.Fc (CIS), the other set contained anti-CD3 or PD-L1.Fc (TRANS). Inhibition through PD-1 was only observed under conditions where both PD-1 and TcR were engaged by ligands on the same surface (CIS). At all bead:cell ratios tested, no inhibition was observed in conditions where TCR and PD-1 signals were delivered on separate surfaces (TRANS).

To rule out steric hindrance in the TRANS experiments, similar assays were set up using anti-CD3 antibody and B7.2.Fc. In these assays, B7 costimulation of T cell responses was observed in both CIS and TRANS conditions. Altogether, these findings demonstrate that PD-1 proximity to TCR is required for the receptor modulator function on T cell activation. Therefore, to modulate a T cell response, both activating and inhibitory signals must emanate from the same surface whether the surface is that of a cell or a bead.

Example 9

Blockage of PD-1 Engagement by Antibody Results in Enhanced Proliferation

For assessing effect of soluble anti-PD-1 antibody on proliferation, CD4+ T cells were pre-activated for 48 hours with anti-CD3/anti-CD28-coated beads, harvested, and restimulated with the indicated concentration of PHA plus 10 ng/ml IL-2 in the presence of PD1-17, J110, or control IgG. Each of the antibodies was added at various concentrations at initiation of the culture. Proliferation was measured at 72 hr.

Figure 6:
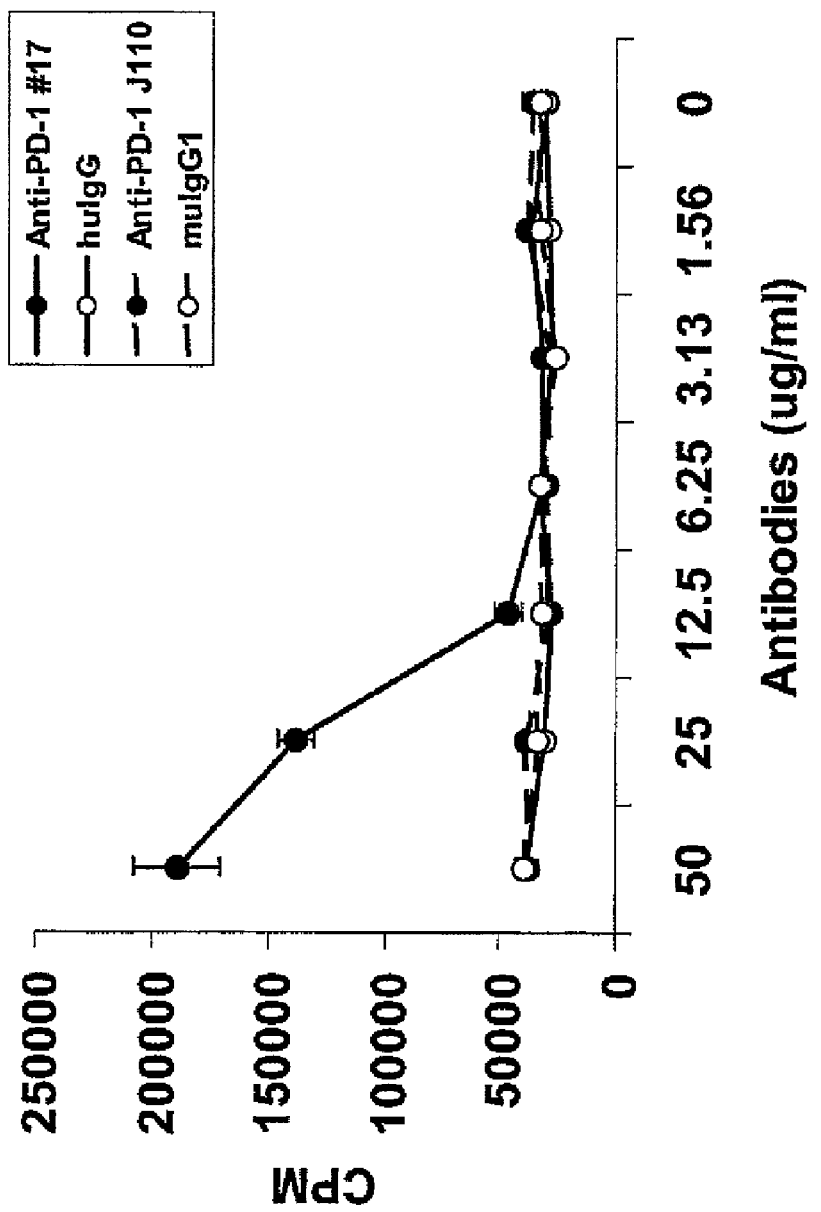
FIG. 6 demonstrates enhanced proliferation of primary T cells by PD1-17 in a soluble form.

The results demonstrate that PD1-17 (FIG. 6) and PD1-35 (data not shown) enhanced proliferation of primary T cells. The control antibody J110 did not enhance in vitro T cell responses. Selected anti-PD1 antibodies, as exemplified by PD1-17 and PD-35, inhibit the interaction of PD-1 with its natural ligands and thereby block delivery of a negative signal. The blockade of the negative signal also results in enhanced proliferation and IL-2 production.

Example 10

Treatment of Disorders

Modulation of immune response regulated by PD-1 is useful in instances where an immunosuppressive effect or augmentation of immune response is desired. This example describes the use of PD-1 antibodies as PD-1 agonists or antagonists to treat a subject at disease onset or having an established immune disorder or cancer, respectively.

Subjects at risk for or afflicted with cancer may be in need of immune response augmentation would benefit from treatment with a PD-1 antagonist, such as an anti-PD-1 antibody of the present invention in a soluble form. Most commonly, antibodies are administered in an outpatient setting by weekly administration at about 0.1-10 mg/kg dose by slow intravenous (IV) infusion. The appropriate therapeutically effective dose of an antagonist is selected by a treating clinician and would range approximately from 1 µg/kg to 20 mg/kg, from 1 µg/kg to 10 mg/kg, from 1 µg/kg to 1 mg/kg, from 10 µg/kg to 1 mg/kg, from 10 µg/kg to 100 µg/kg, from 100 µg to 1 mg/kg, and from 500 µg/kg to 5 mg/kg.

The antibodies are also used to prevent and/or to reduce severity and/or symptoms of diseases or conditions that involve an aberrant or undesirable immune response, such as in autoimmune disorders exemplified below.

Multiple sclerosis (MS) is a central nervous system disease that is characterized by inflammation and loss of myelin sheaths. In the experimental autoimmune encephalitis (EAE) mouse model for multiple sclerosis (Tuohy et al. (J. Immunol. (1988) 141: 1126-1130), Sobel et al. (J. Immunol. (1984) 132: 2393-2401), and Traugott (Cell Immunol. (1989) 119: 114-129), treatment of mice with a PD-1 agonist prior (and continuously) to EAE induction is expected to prevent or delay the onset of MS.

Arthritis is a disease characterized by inflammation in the joints. In the collagen induced arthritis (CIA) mouse model for rheumatoid arthritis (Courtenay et al. (Nature (1980) 283: 666-628) and Williams et al. (Immunol. (1995) 84: 433-439)), treatment with a PD-1 agonist is expected to prevent or treat rheumatoid arthritis (RA) or other arthritic diseases.

Systemic Lupus Erythematosis (SLE) is an autoimmune disease characterized by the presence of autoantibodies. The antibodies and compositions of this invention can be used as PD-1 agonists to inhibit activities of autoreactive T cells and B cells, and prevent or treat SLE or related diseases in NZB X NZW mice (a mouse model for SLE) (Immunologic Defects in Laboratory Animals, Gershwin et al. eds., Plenum Press, 1981) or in humans.

It is anticipated that PD-1 antibodies of the invention would be administered as PD-1 agonists in ex vivo therapy with a frequency of one per month or less. Treatment duration could range between one month and several years.

To test the clinical efficacy of antibodies in humans, individuals with melanoma, prostate cancer, RA, SLE, MS, type I diabetes, are identified and randomized to a treatment group. Treatment groups include a placebo group and one to three groups treated with a PD-1 agonist (different doses). Individuals are followed prospectively for one to three years. It is anticipated that individuals receiving treatment would exhibit an improvement.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

The invention claimed is:

1. An isolated nucleic acid encoding an antibody comprising:
   (i) a $V_H$ domain that comprises three CDRs having the amino acid sequences as set out in:
      (a) SEQ ID NOs: 23, 24, and 25,
      (b) SEQ ID NOs: 29, 30, and 31,
      (c) SEQ ID NOs: 35, 36, and 37, or
      (d) SEQ ID NOs: 50, 51, and 52; or
   (ii) a $V_L$ domain that comprises three CDRs having the amino acid sequences as set out in:
      (e) SEQ ID NOs: 26, 27, and 28,
      (f) SEQ ID NOs: 32, 33, and 34,
      (g) SEQ ID NOs: 38, 39, and 40, or
      (h) SEQ ID NOs: 53, 54, and 55,
wherein the antibody specifically binds an epitope within the extracellular domain of human or mouse PD1.

2. An expression vector comprising the nucleic acid of claim 1.

3. An isolated host cell comprising the vector of claim 2.

4. The nucleic acid of claim 1, wherein the $V_H$ domain comprises the amino acid sequence SEQ ID NO:6, 10, 14, or 47; and the $V_L$ domain comprises the amino acid sequence SEQ ID NO:8, 12, 16, or 49.

5. The nucleic acid of claim 4, wherein the nucleic acid comprises a nucleotide sequence selected from the group consisting of
   (a) SEQ ID NOs: 5, 9, 13, and 46; or
   (b) SEQ ID NOs: 9, 11, 15, and 48.

6. A method of making an antibody that specifically binds with PD-1, the method comprises: (a) providing the expression vector of claim 2; (b) expressing the antibody encoded by the expression vector in a host cell; and (c) recovering the antibody.

* * * * *